US011786272B2

(12) United States Patent
Khairkhahan et al.

(10) Patent No.: US 11,786,272 B2
(45) Date of Patent: *Oct. 17, 2023

(54) PACEMAKER RETRIEVAL SYSTEMS AND METHODS

(71) Applicant: Pacesetter, Inc., Sylmar, CA (US)

(72) Inventors: Alexander Khairkhahan, Palo Alto, CA (US); Alan Klenk, San Jose, CA (US); Thomas Blake Eby, Mountain View, CA (US)

(73) Assignee: PACESETTER, INC., Sylmar, CA (US)

( * ) Notice: Subject to any disclaimer, the term of this patent is extended or adjusted under 35 U.S.C. 154(b) by 197 days.

This patent is subject to a terminal disclaimer.

(21) Appl. No.: 17/344,473

(22) Filed: Jun. 10, 2021

(65) Prior Publication Data

US 2021/0298788 A1 Sep. 30, 2021

Related U.S. Application Data

(63) Continuation of application No. 16/214,709, filed on Dec. 10, 2018, now Pat. No. 11,058,457, which is a
(Continued)

(51) Int. Cl.
*A61B 17/34* (2006.01)
*A61B 17/221* (2006.01)
(Continued)

(52) U.S. Cl.
CPC ........ *A61B 17/3468* (2013.01); *A61B 17/221* (2013.01); *A61N 1/3756* (2013.01);
(Continued)

(58) Field of Classification Search
CPC ............ A61B 17/221; A61B 17/32056; A61B 17/3468; A61B 2017/22035;
(Continued)

(56) References Cited

U.S. PATENT DOCUMENTS 1,340,250 A 5/1920 Pruyn
2,664,324 A 12/1953 Gunnar et al.
(Continued)

FOREIGN PATENT DOCUMENTS

EP 1741465 A1 1/2007
JP 04-506167 A 10/1992
(Continued)

OTHER PUBLICATIONS

Amendment Filed Apr. 21, 2015; Related U.S. Appl. No. 13/324,802.
(Continued)

*Primary Examiner* — Sarah W Aleman
(74) *Attorney, Agent, or Firm* — WOMBLE BOND DICKINSON (US) LLP

(57) ABSTRACT

A catheter system for retrieving a leadless cardiac pacemaker from a patient is provided. The cardiac pacemaker can include a docking or retrieval feature configured to be grasped by the catheter system. In some embodiments, the retrieval catheter can include a snare configured to engage the retrieval feature of the pacemaker. The retrieval catheter can include a torque shaft selectively connectable to a docking cap and be configured to apply rotational torque to a pacemaker to be retrieved. Methods of delivering the leadless cardiac pacemaker with the delivery system are also provided.

20 Claims, 19 Drawing Sheets

Related U.S. Application Data continuation of application No. 14/816,302, filed on Aug. 3, 2015, now Pat. No. 10,188,425, which is a continuation of application No. 13/324,802, filed on Dec. 13, 2011, now Pat. No. 9,126,032.

(60) Provisional application No. 61/422,622, filed on Dec. 13, 2010.

(51) Int. Cl.
| | |
|---|---|
| *A61N 1/375* | (2006.01) |
| *A61N 1/05* | (2006.01) |
| *A61B 17/3205* | (2006.01) |
| *A61N 1/362* | (2006.01) |
| *A61N 1/372* | (2006.01) |
| *A61B 17/22* | (2006.01) |
| *A61B 17/00* | (2006.01) |
| *A61M 25/00* | (2006.01) |

(52) U.S. Cl.
CPC .......... *A61B 17/32056* (2013.01); *A61B 2017/00358* (2013.01); *A61B 2017/22035* (2013.01); *A61M 25/0082* (2013.01); *A61N 1/059* (2013.01); *A61N 1/0573* (2013.01); *A61N 1/362* (2013.01); *A61N 1/37205* (2013.01); *A61N 2001/0578* (2013.01)

(58) Field of Classification Search
CPC ............ A61B 2017/2215; A61N 1/057; A61N 1/0587; A61N 2001/0578
See application file for complete search history.

(56) References Cited

U.S. PATENT DOCUMENTS

| | | |
|---|---|---|
| 3,199,508 A | 8/1965 | Roth |
| 3,212,496 A | 10/1965 | Preston |
| 3,218,638 A | 11/1965 | Honig |
| 3,241,556 A | 3/1966 | Zacouto |
| 3,478,746 A | 11/1969 | Greatbatch |
| 3,603,881 A | 9/1971 | Thornton |
| 3,727,616 A | 4/1973 | Lenzkes |
| 3,757,778 A | 9/1973 | Graham |
| 3,823,708 A | 7/1974 | Lawhorn |
| 3,828,790 A | 8/1974 | Curtiss et al. |
| 3,830,228 A | 8/1974 | Foner |
| 3,835,864 A | 9/1974 | Rasor et al. |
| 3,836,798 A | 9/1974 | Greatbatch |
| 3,870,051 A | 3/1975 | Brindley |
| 3,872,251 A | 3/1975 | Auerbach et al. |
| 3,905,364 A | 9/1975 | Cudahy et al. |
| 3,940,692 A | 2/1976 | Neilson |
| 3,943,926 A | 3/1976 | Arvizu Barragan |
| 3,946,744 A | 3/1976 | Auerbach |
| 3,952,750 A | 4/1976 | Mirowski et al. |
| 4,027,663 A | 6/1977 | Fischler et al. |
| 4,072,154 A | 2/1978 | Anderson et al. |
| 4,083,366 A | 4/1978 | Gombrich et al. |
| 4,102,344 A | 7/1978 | Conway et al. |
| 4,146,029 A | 3/1979 | Ellinwood, Jr. |
| 4,151,513 A | 4/1979 | Barthel et al. |
| 4,151,540 A | 4/1979 | Sander et al. |
| 4,152,540 A | 5/1979 | Brown et al. |
| 4,173,221 A | 11/1979 | McLaughlin et al. |
| 4,187,854 A | 2/1980 | Citron et al. |
| 4,210,149 A | 7/1980 | Heilman et al. |
| RE30,366 E | 8/1980 | Rasor et al. |
| 4,223,678 A | 9/1980 | Langer et al. |
| 4,250,888 A | 2/1981 | Grosskopf |
| 4,256,115 A | 3/1981 | Bilitch |
| 4,296,756 A | 10/1981 | Dunning et al. |
| 4,310,000 A | 1/1982 | Lindemans |
| 4,318,412 A | 3/1982 | Stanly et al. |
| 4,336,810 A | 6/1982 | Anderson et al. |
| 4,350,169 A | 9/1982 | Dutcher et al. |
| 4,374,382 A | 2/1983 | Markowitz |
| 4,406,288 A | 9/1983 | Horwinski et al. |
| 4,411,271 A | 10/1983 | Markowitz |
| 4,418,695 A | 12/1983 | Buffet |
| 4,424,551 A | 1/1984 | Stevenson et al. |
| 4,428,378 A | 1/1984 | Anderson et al. |
| 4,440,173 A | 4/1984 | Hudziak et al. |
| 4,442,840 A | 4/1984 | Wojciechowicz, Jr. |
| 4,453,162 A | 6/1984 | Money et al. |
| 4,458,692 A | 7/1984 | Simson |
| 4,481,950 A | 11/1984 | Duggan |
| 4,513,743 A | 4/1985 | Van et al. |
| 4,516,579 A | 5/1985 | Irnich |
| 4,522,208 A | 6/1985 | Buffet |
| 4,524,774 A | 6/1985 | Hildebrandt |
| 4,531,527 A | 7/1985 | Reinhold et al. |
| 4,543,955 A | 10/1985 | Schroeppel |
| 4,550,370 A | 10/1985 | Baker |
| 4,552,127 A | 11/1985 | Schiff |
| 4,552,154 A | 11/1985 | Hartlaub |
| 4,562,846 A | 1/1986 | Cox et al. |
| 4,582,056 A * | 4/1986 | McCorkle, Jr. ........ A61B 17/29 606/1 |
| 4,586,508 A | 5/1986 | Batina et al. |
| 4,606,352 A | 8/1986 | Geddes et al. |
| 4,607,639 A | 8/1986 | Tanagho et al. |
| 4,612,934 A | 9/1986 | Borkan |
| 4,625,730 A | 12/1986 | Fountain et al. |
| 4,665,906 A | 5/1987 | Jervis |
| 4,679,144 A | 7/1987 | Cox et al. |
| 4,681,111 A | 7/1987 | Silvian |
| 4,681,117 A | 7/1987 | Brodman et al. |
| 4,702,253 A | 10/1987 | Nappholz et al. |
| 4,719,920 A | 1/1988 | Alt et al. |
| 4,722,342 A | 2/1988 | Amundson |
| 4,750,495 A | 6/1988 | Moore et al. |
| 4,763,340 A | 8/1988 | Yoneda et al. |
| 4,763,655 A | 8/1988 | Wirtzfeld et al. |
| 4,787,389 A | 11/1988 | Tarjan |
| 4,791,931 A | 12/1988 | Slate |
| 4,793,353 A | 12/1988 | Borkan |
| 4,794,532 A | 12/1988 | Leckband et al. |
| 4,802,481 A | 2/1989 | Schroeppel |
| 4,809,697 A | 3/1989 | Causey et al. |
| 4,827,940 A | 5/1989 | Mayer et al. |
| 4,830,006 A | 5/1989 | Haluska et al. |
| 4,844,076 A | 7/1989 | Lesho et al. |
| 4,846,195 A | 7/1989 | Alt |
| 4,858,610 A | 8/1989 | Callaghan et al. |
| 4,860,750 A | 8/1989 | Frey et al. |
| 4,875,483 A | 10/1989 | Vollmann et al. |
| 4,880,004 A | 11/1989 | Baker et al. |
| 4,883,064 A | 11/1989 | Olson et al. |
| 4,886,064 A | 12/1989 | Strandberg |
| 4,896,068 A | 1/1990 | Nilsson |
| 4,903,701 A | 2/1990 | Moore et al. |
| 4,905,708 A | 3/1990 | Davies |
| 4,926,863 A | 5/1990 | Alt |
| 4,974,589 A | 12/1990 | Sholder |
| 4,987,897 A | 1/1991 | Funke |
| 4,995,390 A | 2/1991 | Cook et al. |
| 5,010,887 A | 4/1991 | Thornander |
| 5,012,806 A | 5/1991 | De Bellis |
| 5,014,701 A | 5/1991 | Pless et al. |
| 5,040,533 A | 8/1991 | Fearnot |
| 5,040,534 A | 8/1991 | Mann et al. |
| 5,040,536 A | 8/1991 | Riff |
| 5,042,497 A | 8/1991 | Shapland |
| 5,052,399 A | 10/1991 | Olive et al. |
| 5,058,581 A | 10/1991 | Silvian |
| 5,065,759 A | 11/1991 | Begemann et al. |
| 5,076,270 A | 12/1991 | Stutz, Jr. |
| 5,076,272 A | 12/1991 | Ferek-Petric |
| 5,085,224 A | 2/1992 | Galen et al. |
| 5,086,772 A | 2/1992 | Larnard et al. |
| 5,088,488 A | 2/1992 | Markowitz et al. |
| 5,095,903 A | 3/1992 | DeBellis |
| 5,098,440 A | 3/1992 | Hillstead |

(56) References Cited

U.S. PATENT DOCUMENTS

| | | | |
|---|---|---|---|
| 5,109,845 A | 5/1992 | Yuuchi et al. | |
| 5,111,816 A | 5/1992 | Pless et al. | |
| 5,113,859 A | 5/1992 | Funke | |
| 5,113,869 A | 5/1992 | Nappholz et al. | |
| 5,133,350 A | 7/1992 | Duffin | |
| 5,133,733 A | 7/1992 | Rasmussen et al. | |
| 5,135,004 A | 8/1992 | Adams et al. | |
| 5,170,784 A | 12/1992 | Ramon et al. | |
| 5,170,802 A | 12/1992 | Mehra | |
| 5,171,233 A | 12/1992 | Amplatz et al. | |
| 5,179,947 A | 1/1993 | Meyerson et al. | |
| 5,179,962 A * | 1/1993 | Dutcher | A61N 1/0573 607/128 |
| 5,184,616 A | 2/1993 | Weiss | |
| 5,193,539 A | 3/1993 | Schulman et al. | |
| 5,193,540 A | 3/1993 | Schulman et al. | |
| 5,193,550 A | 3/1993 | Duffin | |
| 5,197,978 A | 3/1993 | Hess | |
| 5,217,010 A | 6/1993 | Tsitlik et al. | |
| 5,231,989 A * | 8/1993 | Middleman | A61M 25/0147 604/95.01 |
| 5,247,945 A | 9/1993 | Heinze et al. | |
| 5,259,394 A | 11/1993 | Bens | |
| 5,267,150 A | 11/1993 | Wilkinson | |
| 5,282,841 A | 2/1994 | Szyszkowski | |
| 5,284,136 A | 2/1994 | Hauck et al. | |
| 5,291,902 A | 3/1994 | Carman | |
| 5,300,093 A | 4/1994 | Koestner et al. | |
| 5,304,206 A | 4/1994 | Baker et al. | |
| 5,304,209 A | 4/1994 | Adams et al. | |
| 5,313,953 A | 5/1994 | Yomtov et al. | |
| 5,318,596 A | 6/1994 | Barreras et al. | |
| 5,331,966 A | 7/1994 | Bennett et al. | |
| 5,333,095 A | 7/1994 | Stevenson et al. | |
| 5,336,244 A | 8/1994 | Weijand | |
| 5,342,401 A | 8/1994 | Spano et al. | |
| 5,354,317 A | 10/1994 | Alt | |
| 5,358,514 A | 10/1994 | Schulman et al. | |
| 5,373,852 A | 12/1994 | Harrison et al. | |
| 5,383,912 A | 1/1995 | Cox et al. | |
| 5,383,915 A | 1/1995 | Adams | |
| 5,404,877 A | 4/1995 | Nolan et al. | |
| 5,405,367 A | 4/1995 | Schulman et al. | |
| 5,406,444 A | 4/1995 | Selfried et al. | |
| 5,411,532 A | 5/1995 | Mortazavi | |
| 5,411,535 A | 5/1995 | Fujii et al. | |
| 5,411,537 A | 5/1995 | Munshi et al. | |
| 5,417,222 A | 5/1995 | Dempsey et al. | |
| 5,419,337 A | 5/1995 | Dempsey et al. | |
| 5,431,171 A | 7/1995 | Harrison et al. | |
| 5,446,447 A | 8/1995 | Carney et al. | |
| 5,456,261 A | 10/1995 | Luczyk | |
| 5,466,246 A | 11/1995 | Silvian | |
| 5,469,857 A | 11/1995 | Laurent et al. | |
| 5,480,415 A | 1/1996 | Cox et al. | |
| 5,481,262 A | 1/1996 | Urbas et al. | |
| 5,522,876 A | 6/1996 | Rusink | |
| 5,531,779 A | 7/1996 | Dahl et al. | |
| 5,531,781 A | 7/1996 | Alferness et al. | |
| 5,531,783 A | 7/1996 | Giele et al. | |
| 5,539,775 A | 7/1996 | Tuttle et al. | |
| 5,549,654 A | 8/1996 | Powell | |
| 5,549,659 A | 8/1996 | Johansen et al. | |
| 5,551,427 A | 9/1996 | Altman | |
| 5,556,421 A | 9/1996 | Prutchi et al. | |
| 5,562,717 A | 10/1996 | Tippey et al. | |
| 5,571,143 A | 11/1996 | Hoegnelid et al. | |
| 5,571,148 A | 11/1996 | Loeb et al. | |
| 5,579,775 A | 12/1996 | Dempsey et al. | |
| 5,586,556 A | 12/1996 | Spivey et al. | |
| 5,591,217 A | 1/1997 | Barreras | |
| 5,598,848 A | 2/1997 | Swanson et al. | |
| 5,649,952 A | 7/1997 | Lam | |
| 5,650,759 A | 7/1997 | Hittman et al. | |
| 5,654,984 A | 8/1997 | Hershbarger et al. | |
| 5,662,689 A | 9/1997 | Elsberry et al. | |
| 5,669,391 A | 9/1997 | Williams | |
| 5,674,259 A | 10/1997 | Gray | |
| 5,676,153 A | 10/1997 | Smith et al. | |
| 5,693,076 A | 12/1997 | Kaemmerer | |
| 5,694,940 A | 12/1997 | Unger et al. | |
| 5,694,952 A | 12/1997 | Lidman et al. | |
| 5,697,958 A | 12/1997 | Paul et al. | |
| 5,702,427 A | 12/1997 | Ecker et al. | |
| 5,709,704 A | 1/1998 | Nott et al. | |
| 5,725,559 A | 3/1998 | Alt et al. | |
| 5,728,154 A | 3/1998 | Crossett et al. | |
| 5,730,143 A | 3/1998 | Schwarzberg | |
| 5,735,880 A | 4/1998 | Prutchi et al. | |
| 5,738,102 A | 4/1998 | Lemelson | |
| 5,740,811 A | 4/1998 | Hedberg et al. | |
| 5,741,314 A | 4/1998 | Daly et al. | |
| 5,766,231 A | 6/1998 | Erickson et al. | |
| 5,792,205 A | 8/1998 | Alt et al. | |
| 5,807,399 A * | 9/1998 | Laske | A61N 1/057 606/108 |
| 5,810,735 A | 9/1998 | Halperin et al. | |
| 5,814,076 A | 9/1998 | Brownlee | |
| 5,814,087 A | 9/1998 | Renirie | |
| 5,814,089 A | 9/1998 | Stokes et al. | |
| 5,817,104 A | 10/1998 | Bilitz et al. | |
| 5,824,016 A | 10/1998 | Ekwall | |
| 5,871,451 A | 2/1999 | Unger et al. | |
| 5,876,353 A | 3/1999 | Riff | |
| 5,876,425 A | 3/1999 | Gord et al. | |
| 5,891,178 A | 4/1999 | Mann et al. | |
| 5,899,928 A | 5/1999 | Sholder et al. | |
| 5,935,079 A | 8/1999 | Swanson et al. | |
| 5,954,761 A | 9/1999 | Machek et al. | |
| 5,957,861 A | 9/1999 | Combs et al. | |
| 5,984,861 A | 11/1999 | Crowley | |
| 5,987,352 A | 11/1999 | Klein et al. | |
| 5,995,876 A | 11/1999 | Kruse et al. | |
| 5,999,857 A | 12/1999 | Weijand et al. | |
| 6,002,969 A | 12/1999 | Machek et al. | |
| 6,004,269 A | 12/1999 | Crowley et al. | |
| 6,061,596 A | 5/2000 | Richmond et al. | |
| 6,076,016 A | 6/2000 | Feierbach | |
| 6,077,274 A | 6/2000 | Ouchi et al. | |
| 6,080,187 A | 6/2000 | Alt et al. | |
| 6,086,577 A | 7/2000 | Ken et al. | |
| 6,093,146 A | 7/2000 | Filangeri | |
| 6,096,065 A | 8/2000 | Crowley | |
| 6,099,534 A | 8/2000 | Bates et al. | |
| 6,102,874 A | 8/2000 | Stone et al. | |
| 6,112,116 A | 8/2000 | Fischell et al. | |
| 6,115,628 A | 9/2000 | Stadler et al. | |
| 6,115,630 A | 9/2000 | Stadler et al. | |
| 6,115,636 A | 9/2000 | Ryan | |
| 6,119,031 A | 9/2000 | Crowley | |
| 6,125,290 A | 9/2000 | Miesel | |
| 6,125,291 A | 9/2000 | Miesel et al. | |
| 6,128,526 A | 10/2000 | Stadler et al. | |
| 6,129,751 A | 10/2000 | Lucchesi et al. | |
| 6,132,390 A | 10/2000 | Cookston et al. | |
| 6,132,456 A | 10/2000 | Sommer et al. | |
| 6,134,459 A | 10/2000 | Roberts et al. | |
| 6,134,470 A | 10/2000 | Hartlaub | |
| 6,139,510 A | 10/2000 | Palermo | |
| 6,141,584 A | 10/2000 | Rockwell et al. | |
| 6,141,588 A | 10/2000 | Cox et al. | |
| 6,141,592 A | 10/2000 | Pauly | |
| 6,144,866 A | 11/2000 | Miesel et al. | |
| 6,148,230 A | 11/2000 | Kenknight | |
| 6,152,882 A | 11/2000 | Prutchi | |
| 6,163,723 A | 12/2000 | Roberts et al. | |
| 6,164,284 A | 12/2000 | Schulman et al. | |
| 6,167,310 A | 12/2000 | Grevious | |
| 6,178,349 B1 | 1/2001 | Kieval | |
| 6,178,356 B1 | 1/2001 | Chastain et al. | |
| 6,185,443 B1 | 2/2001 | Crowley | |
| 6,185,452 B1 | 2/2001 | Schulman et al. | |
| 6,185,464 B1 | 2/2001 | Bonner et al. | |
| 6,188,932 B1 | 2/2001 | Lindegren | |

(56) References Cited

U.S. PATENT DOCUMENTS

| | | |
|---|---|---|
| 6,190,324 B1 | 2/2001 | Kieval et al. |
| 6,198,952 B1 | 3/2001 | Miesel |
| 6,201,993 B1 | 3/2001 | Kruse et al. |
| 6,208,894 B1 | 3/2001 | Schulman et al. |
| 6,208,900 B1 | 3/2001 | Ecker et al. |
| 6,214,025 B1 | 4/2001 | Thistle et al. |
| 6,223,081 B1 | 4/2001 | Kerver |
| 6,230,059 B1 | 5/2001 | Duffin |
| 6,236,882 B1 | 5/2001 | Lee et al. |
| 6,240,321 B1 | 5/2001 | Janke et al. |
| 6,243,608 B1 | 6/2001 | Pauly et al. |
| 6,248,080 B1 | 6/2001 | Miesel et al. |
| 6,263,245 B1 | 7/2001 | Snell |
| 6,265,100 B1 | 7/2001 | Saaski et al. |
| 6,266,554 B1 | 7/2001 | Hsu et al. |
| 6,266,564 B1 | 7/2001 | Hill et al. |
| 6,272,379 B1 | 8/2001 | Fischell et al. |
| 6,280,409 B1 | 8/2001 | Stone et al. |
| 6,280,451 B1 | 8/2001 | Bates et al. |
| 6,289,229 B1 | 9/2001 | Crowley |
| 6,290,721 B1 | 9/2001 | Heath |
| 6,306,088 B1 | 10/2001 | Krausman et al. |
| 6,310,960 B1 | 10/2001 | Saaski et al. |
| 6,315,721 B2 | 11/2001 | Schulman et al. |
| 6,324,418 B1 | 11/2001 | Crowley et al. |
| 6,324,421 B1 | 11/2001 | Stadler et al. |
| RE37,463 E | 12/2001 | Altman |
| 6,343,227 B1 | 1/2002 | Crowley |
| 6,343,233 B1 | 1/2002 | Werner et al. |
| 6,347,245 B1 | 2/2002 | Lee et al. |
| 6,358,202 B1 | 3/2002 | Arent |
| 6,361,522 B1 | 3/2002 | Scheiner et al. |
| 6,363,282 B1 | 3/2002 | Nichols et al. |
| 6,364,831 B1 | 4/2002 | Crowley |
| 6,370,434 B1 | 4/2002 | Zhang et al. |
| 6,381,492 B1 | 4/2002 | Rockwell et al. |
| 6,381,493 B1 | 4/2002 | Stadler et al. |
| 6,381,494 B1 | 4/2002 | Gilkerson et al. |
| 6,383,209 B1 | 5/2002 | Crowley |
| 6,385,593 B2 | 5/2002 | Linberg |
| 6,386,882 B1 | 5/2002 | Linberg |
| 6,397,100 B2 | 5/2002 | Stadler et al. |
| 6,399,886 B1 | 6/2002 | Avellanet |
| 6,402,689 B1 | 6/2002 | Scarantino et al. |
| 6,405,073 B1 | 6/2002 | Crowley et al. |
| 6,405,083 B1 | 6/2002 | Rockwell et al. |
| 6,409,674 B1 | 6/2002 | Brockway et al. |
| 6,409,675 B1 | 6/2002 | Turcott |
| 6,412,490 B1 | 7/2002 | Lee |
| 6,418,346 B1 | 7/2002 | Nelson et al. |
| 6,423,056 B1 | 7/2002 | Ishikawa et al. |
| 6,424,866 B2 | 7/2002 | Mika et al. |
| 6,428,484 B1 | 8/2002 | Battmer et al. |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,442,433 B1 | 8/2002 | Linberg |
| 6,444,970 B1 | 9/2002 | Barbato |
| 6,445,953 B1 | 9/2002 | Bulkes et al. |
| 6,458,145 B1 | 10/2002 | Ravenscroft et al. |
| 6,459,928 B2 | 10/2002 | Mika et al. |
| 6,459,937 B1 | 10/2002 | Morgan et al. |
| 6,466,820 B1 | 10/2002 | Juran et al. |
| 6,468,263 B1 | 10/2002 | Fischell et al. |
| 6,470,215 B1 | 10/2002 | Kraus et al. |
| 6,471,645 B1 | 10/2002 | Warkentin et al. |
| 6,472,991 B1 | 10/2002 | Schulman et al. |
| 6,477,424 B1 | 11/2002 | Thompson et al. |
| 6,480,733 B1 | 11/2002 | Turcott |
| 6,482,154 B1 | 11/2002 | Haubrich et al. |
| 6,484,055 B1 | 11/2002 | Marcovecchio |
| 6,484,057 B2 | 11/2002 | Ideker et al. |
| 6,490,487 B1 | 12/2002 | Kraus et al. |
| 6,496,715 B1 | 12/2002 | Lee et al. |
| 6,498,951 B1 | 12/2002 | Larson et al. |
| 6,500,168 B1 | 12/2002 | Jellie |
| 6,501,983 B1 | 12/2002 | Natarajan et al. |
| 6,512,949 B1 | 1/2003 | Combs et al. |
| 6,512,959 B1 | 1/2003 | Gomperz et al. |
| 6,522,926 B1 | 2/2003 | Kieval et al. |
| 6,522,928 B2 | 2/2003 | Whitehurst et al. |
| 6,539,257 B1 | 3/2003 | Kenknight |
| 6,542,781 B1 | 4/2003 | Koblish et al. |
| 6,556,860 B1 | 4/2003 | Groenewegen |
| 6,558,321 B1 | 5/2003 | Burd et al. |
| 6,564,807 B1 | 5/2003 | Schulman et al. |
| 6,567,680 B2 | 5/2003 | Swetlik et al. |
| 6,571,120 B2 | 5/2003 | Hutten |
| 6,574,509 B1 | 6/2003 | Kraus et al. |
| 6,574,511 B2 | 6/2003 | Lee |
| 6,580,946 B2 | 6/2003 | Struble |
| 6,580,948 B2 | 6/2003 | Haupert et al. |
| 6,584,351 B1 | 6/2003 | Ekwall |
| 6,584,352 B2 | 6/2003 | Combs et al. |
| 6,589,187 B1 | 7/2003 | Dirnberger et al. |
| 6,592,518 B2 | 7/2003 | Denker et al. |
| 6,594,523 B1 | 7/2003 | Levine |
| 6,597,948 B1 | 7/2003 | Rockwell et al. |
| 6,597,952 B1 | 7/2003 | Mika et al. |
| 6,609,023 B1 | 8/2003 | Fischell et al. |
| 6,611,710 B2 | 8/2003 | Gomperz et al. |
| 6,615,075 B2 | 9/2003 | Mlynash et al. |
| 6,622,043 B1 | 9/2003 | Kraus et al. |
| 6,647,292 B1 | 11/2003 | Bardy et al. |
| 6,648,823 B2 | 11/2003 | Thompson |
| 6,649,078 B2 | 11/2003 | Yu |
| 6,654,638 B1 | 11/2003 | Sweeney |
| 6,658,285 B2 | 12/2003 | Potse et al. |
| 6,658,297 B2 | 12/2003 | Loeb |
| 6,658,301 B2 | 12/2003 | Loeb et al. |
| 6,659,959 B2 | 12/2003 | Brockway et al. |
| 6,669,631 B2 | 12/2003 | Norris et al. |
| 6,681,135 B1 | 1/2004 | Davis et al. |
| 6,684,100 B1 | 1/2004 | Sweeney et al. |
| 6,687,540 B2 | 2/2004 | Marcovecchio |
| 6,687,546 B2 | 2/2004 | Lebel et al. |
| 6,689,117 B2 | 2/2004 | Sweeney et al. |
| 6,690,959 B2 | 2/2004 | Thompson |
| 6,694,191 B2 | 2/2004 | Starkweather et al. |
| 6,695,885 B2 | 2/2004 | Schulman et al. |
| 6,697,672 B2 | 2/2004 | Andersson |
| 6,697,676 B2 | 2/2004 | Dahl et al. |
| 6,697,677 B2 | 2/2004 | Dahl et al. |
| 6,699,200 B2 | 3/2004 | Cao et al. |
| 6,702,857 B2 | 3/2004 | Brauker et al. |
| 6,704,602 B2 | 3/2004 | Berg et al. |
| 6,711,440 B2 | 3/2004 | Deal et al. |
| 6,716,238 B2 | 4/2004 | Elliott |
| 6,721,597 B1 | 4/2004 | Bardy et al. |
| 6,728,572 B2 | 4/2004 | Hsu et al. |
| 6,728,574 B2 | 4/2004 | Ujhelyi et al. |
| 6,728,576 B2 | 4/2004 | Thompson et al. |
| 6,731,976 B2 | 5/2004 | Penn et al. |
| 6,731,979 B2 | 5/2004 | Macdonald |
| 6,733,485 B1 | 5/2004 | Whitehurst et al. |
| 6,735,474 B1 | 5/2004 | Loeb et al. |
| 6,735,475 B1 | 5/2004 | Whitehurst et al. |
| 6,738,670 B1 | 5/2004 | Almendinger et al. |
| 6,741,877 B1 | 5/2004 | Shults et al. |
| 6,741,886 B2 | 5/2004 | Yonce |
| 6,746,404 B2 | 6/2004 | Schwartz |
| 6,754,538 B2 | 6/2004 | Linberg |
| 6,760,620 B2 | 7/2004 | Sippens Groenewegen |
| 6,764,446 B2 | 7/2004 | Wolinsky et al. |
| 6,768,923 B2 | 7/2004 | Ding et al. |
| 6,783,499 B2 | 8/2004 | Schwartz |
| 6,785,576 B2 | 8/2004 | Verness |
| 6,786,860 B2 | 9/2004 | Maltan et al. |
| 6,792,314 B2 | 9/2004 | Byers et al. |
| 6,799,069 B2 | 9/2004 | Weiner et al. |
| 6,804,559 B1 | 10/2004 | Kraus et al. |
| 6,804,561 B2 | 10/2004 | Stover |
| 6,809,507 B2 | 10/2004 | Morgan et al. |
| 6,811,533 B2 | 11/2004 | Lebel et al. |

(56) References Cited

U.S. PATENT DOCUMENTS

| | | |
|---|---|---|
| 6,813,519 B2 | 11/2004 | Lebel et al. |
| 6,821,154 B1 | 11/2004 | Canfield et al. |
| 6,823,217 B2 | 11/2004 | Rutten et al. |
| 6,824,512 B2 | 11/2004 | Warkentin et al. |
| 6,829,508 B2 | 12/2004 | Schulman et al. |
| 6,839,596 B2 | 1/2005 | Nelson et al. |
| 6,848,052 B2 | 1/2005 | Hamid et al. |
| 6,850,801 B2 | 2/2005 | Kieval et al. |
| 6,856,835 B2 | 2/2005 | Bardy et al. |
| 6,862,465 B2 | 3/2005 | Shults et al. |
| 6,862,480 B2 | 3/2005 | Cohen et al. |
| 6,865,420 B1 | 3/2005 | Kroll |
| 6,869,404 B2 | 3/2005 | Schulhauser et al. |
| 6,871,099 B1 | 3/2005 | Whitehurst et al. |
| 6,878,112 B2 | 4/2005 | Linberg et al. |
| 6,879,695 B2 | 4/2005 | Maltan et al. |
| 6,879,855 B2 | 4/2005 | Schulman et al. |
| 6,882,875 B1 | 4/2005 | Crowley |
| 6,889,081 B2 | 5/2005 | Hsu |
| 6,893,395 B1 | 5/2005 | Kraus et al. |
| 6,895,279 B2 | 5/2005 | Loeb et al. |
| 6,895,281 B1 | 5/2005 | Amundson et al. |
| 6,896,651 B2 | 5/2005 | Gross et al. |
| 6,897,788 B2 | 5/2005 | Khair et al. |
| 6,901,294 B1 | 5/2005 | Whitehurst et al. |
| 6,901,296 B1 | 5/2005 | Whitehurst et al. |
| 6,907,285 B2 | 6/2005 | Denker et al. |
| 6,907,293 B2 | 6/2005 | Grill et al. |
| 6,912,420 B2 | 6/2005 | Scheiner et al. |
| 6,917,833 B2 | 7/2005 | Denker et al. |
| 6,925,328 B2 | 8/2005 | Foster et al. |
| 6,931,327 B2 | 8/2005 | Goode et al. |
| 6,999,821 B2 | 2/2006 | Jenney et al. |
| 7,001,372 B2 | 2/2006 | Richter |
| 7,004,176 B2 | 2/2006 | Lau |
| 7,023,359 B2 | 4/2006 | Goetz et al. |
| 7,027,876 B2 | 4/2006 | Casavant et al. |
| 7,146,222 B2 | 12/2006 | Boling |
| 7,146,225 B2 | 12/2006 | Guenst et al. |
| 7,164,950 B2 | 1/2007 | Kroll et al. |
| 7,181,505 B2 | 2/2007 | Haller et al. |
| 7,187,971 B2 | 3/2007 | Sommer et al. |
| 7,200,437 B1 | 4/2007 | Nabutovsky et al. |
| 7,212,870 B1 | 5/2007 | Helland |
| 7,277,754 B2 | 10/2007 | McCabe et al. |
| 7,289,853 B1 | 10/2007 | Campbell et al. |
| 7,363,090 B2 | 4/2008 | Halperin et al. |
| 7,558,631 B2 | 7/2009 | Cowan et al. |
| 7,565,195 B1 | 7/2009 | Kroll et al. |
| 7,616,991 B2 | 11/2009 | Mann et al. |
| 7,630,767 B1 | 12/2009 | Poore et al. |
| 7,634,313 B1 | 12/2009 | Kroll et al. |
| 7,848,823 B2 | 12/2010 | Drasler et al. |
| 7,937,148 B2 | 5/2011 | Jacobson |
| 7,945,333 B2 | 5/2011 | Jacobson |
| 7,998,163 B2 | 8/2011 | Salahieh et al. |
| 8,010,209 B2 | 8/2011 | Jacobson |
| 8,103,361 B2 | 1/2012 | Moser |
| 8,986,362 B2 | 3/2015 | Snow et al. |
| 9,126,032 B2 | 9/2015 | Khairkhahan et al. |
| 10,188,425 B2 | 1/2019 | Khairkhahan et al. |
| 2001/0031999 A1 | 10/2001 | Carter et al. |
| 2002/0032467 A1 | 3/2002 | Shemer et al. |
| 2002/0065543 A1* | 5/2002 | Gomperz ............ A61N 1/057 607/1 |
| 2002/0077686 A1 | 6/2002 | Westlund et al. |
| 2002/0116028 A1 | 8/2002 | Greatbatch et al. |
| 2002/0147488 A1 | 10/2002 | Doan et al. |
| 2003/0078618 A1 | 4/2003 | Fey et al. |
| 2003/0105506 A1 | 6/2003 | Krishnan et al. |
| 2003/0141995 A1 | 7/2003 | Lin |
| 2003/0158584 A1 | 8/2003 | Cates et al. |
| 2003/0163184 A1 | 8/2003 | Scheiner et al. |
| 2003/0199941 A1 | 10/2003 | Nielsen et al. |
| 2004/0011366 A1 | 1/2004 | Schulman et al. |
| 2004/0059392 A1 | 3/2004 | Parramon et al. |
| 2004/0116939 A1 | 6/2004 | Goode |
| 2004/0133242 A1 | 7/2004 | Chapman et al. |
| 2004/0138693 A1 | 7/2004 | Eskuri et al. |
| 2004/0143262 A1 | 7/2004 | Visram et al. |
| 2004/0147973 A1 | 7/2004 | Hauser |
| 2004/0158124 A1 | 8/2004 | Okada |
| 2004/0167587 A1 | 8/2004 | Thompson |
| 2004/0172116 A1 | 9/2004 | Seifert et al. |
| 2004/0193223 A1 | 9/2004 | Kramer et al. |
| 2004/0220637 A1 | 11/2004 | Zdeblick et al. |
| 2004/0249417 A1 | 12/2004 | Ransbury et al. |
| 2004/0260349 A1 | 12/2004 | Stroebel |
| 2005/0038474 A1 | 2/2005 | Wool |
| 2005/0038491 A1 | 2/2005 | Haack |
| 2005/0043765 A1 | 2/2005 | Williams et al. |
| 2005/0075682 A1 | 4/2005 | Schulman et al. |
| 2005/0096702 A1 | 5/2005 | Denker et al. |
| 2005/0131478 A1 | 6/2005 | Kim et al. |
| 2005/0149138 A1 | 7/2005 | Min et al. |
| 2005/0165465 A1 | 7/2005 | Pianca et al. |
| 2005/0267555 A1 | 12/2005 | Marnfeldt et al. |
| 2005/0288722 A1 | 12/2005 | Eigler et al. |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0105613 A1 | 5/2006 | Carroll |
| 2006/0108335 A1 | 5/2006 | Zhao et al. |
| 2006/0121475 A1 | 6/2006 | Davids et al. |
| 2006/0135999 A1 | 6/2006 | Bodner et al. |
| 2006/0136004 A1 | 6/2006 | Cowan et al. |
| 2006/0161222 A1 | 7/2006 | Haubrich et al. |
| 2006/0235431 A1* | 10/2006 | Goode ............ A61B 17/32002 606/108 |
| 2006/0241705 A1 | 10/2006 | Neumann et al. |
| 2006/0247750 A1 | 11/2006 | Seifert et al. |
| 2006/0282150 A1 | 12/2006 | Olson et al. |
| 2007/0016263 A1 | 1/2007 | Armstrong et al. |
| 2007/0032816 A1 | 2/2007 | O'Connell et al. |
| 2007/0043414 A1 | 2/2007 | Fifer et al. |
| 2007/0055184 A1 | 3/2007 | Echt et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088400 A1 | 4/2007 | Jacobson |
| 2007/0088405 A1 | 4/2007 | Jacobson |
| 2007/0088418 A1 | 4/2007 | Jacobson |
| 2007/0123923 A1 | 5/2007 | Lindstrom et al. |
| 2007/0142709 A1 | 6/2007 | Marton et al. |
| 2007/0156225 A1 | 7/2007 | George et al. |
| 2007/0179552 A1 | 8/2007 | Dennis et al. |
| 2007/0270675 A1 | 11/2007 | Kane et al. |
| 2007/0276004 A1 | 11/2007 | Hirsch et al. |
| 2007/0276444 A1 | 11/2007 | Gelbart et al. |
| 2007/0293904 A1 | 12/2007 | Gelbart et al. |
| 2008/0004535 A1 | 1/2008 | Smits |
| 2008/0021532 A1 | 1/2008 | Kveen et al. |
| 2008/0039738 A1 | 2/2008 | Dinsmoor et al. |
| 2008/0071339 A1 | 3/2008 | Stalker et al. |
| 2008/0086168 A1 | 4/2008 | Cahill |
| 2008/0091255 A1 | 4/2008 | Caparso et al. |
| 2008/0119911 A1 | 5/2008 | Rosero |
| 2008/0221582 A1 | 9/2008 | Gia et al. |
| 2008/0243106 A1 | 10/2008 | Coe et al. |
| 2008/0243218 A1 | 10/2008 | Bottomley et al. |
| 2008/0249558 A1 | 10/2008 | Cahill |
| 2008/0269591 A1 | 10/2008 | Halperin et al. |
| 2009/0018599 A1 | 1/2009 | Hastings et al. |
| 2009/0082827 A1 | 3/2009 | Kveen et al. |
| 2009/0082828 A1 | 3/2009 | Ostroff |
| 2009/0149902 A1 | 6/2009 | Kumar et al. |
| 2009/0163926 A1 | 6/2009 | Sos |
| 2009/0171408 A1 | 7/2009 | Solem |
| 2010/0069983 A1 | 3/2010 | Peacock et al. |
| 2010/0198288 A1 | 8/2010 | Ostroff |
| 2010/0211149 A1 | 8/2010 | Morgan et al. |
| 2010/0249828 A1 | 9/2010 | Mavani et al. |

(56) References Cited

U.S. PATENT DOCUMENTS

| | | |
|---|---|---|
| 2010/0292541 A1 | 11/2010 | Hashiba et al. |
| 2010/0305653 A1 | 12/2010 | Lund et al. |
| 2010/0305656 A1 | 12/2010 | Imran et al. |
| 2010/0312332 A1 | 12/2010 | Forster et al. |
| 2011/0004117 A1 | 1/2011 | Neville et al. |
| 2011/0015729 A1 | 1/2011 | Jimenez et al. |
| 2011/0071586 A1 | 3/2011 | Jacobson |
| 2011/0077708 A1 | 3/2011 | Ostroff |
| 2011/0112548 A1 | 5/2011 | Fifer et al. |
| 2011/0208260 A1 | 8/2011 | Jacobson |
| 2011/0218587 A1 | 9/2011 | Jacobson |
| 2011/0270340 A1 | 11/2011 | Pellegrini et al. |
| 2011/0282423 A1 | 11/2011 | Jacobson |
| 2012/0245665 A1 | 9/2012 | Friedman et al. |
| 2013/0041422 A1 | 2/2013 | Jacobson |

FOREIGN PATENT DOCUMENTS

| | | |
|---|---|---|
| JP | 05-245215 A | 9/1993 |
| JP | 06-507096 A | 8/1994 |
| JP | 2006-516449 A | 7/2006 |
| JP | 2006-526483 A | 11/2006 |
| WO | 93/12714 A1 | 7/1993 |
| WO | 99/16363 A1 | 4/1999 |
| WO | 00/59376 A1 | 10/2000 |
| WO | 02/34333 A2 | 5/2002 |
| WO | 03/32807 A2 | 4/2003 |
| WO | 2004/012811 A1 | 2/2004 |
| WO | 2006/065394 A1 | 6/2006 |
| WO | 2007/046768 A1 | 4/2007 |
| WO | 2007/047681 A2 | 4/2007 |
| WO | 2007/059386 A2 | 5/2007 |
| WO | 2008/058265 A2 | 5/2008 |
| WO | 2010/088116 A1 | 8/2010 |
| WO | 2012/082735 A1 | 6/2012 |

OTHER PUBLICATIONS

Beeby et al.; Micromachined silicon generator for harvesting power from vibrations; (Proceedings) PowerMEMS 2004; Kyoto, Japan; pp. 104-107; Nov. 28-30, 2004.
Bordacher et al.; Impact and prevention of far-field sensing in fallback mode switches; PACE; vol. 26 (pt. II); pp. 206-209; Jan. 2003.
Brandt et al.; Far-field QRS complex sensing: prevalence and timing with bipolar atrial leads; PACE; vol. 23; pp. 315-320; Mar. 2000.
Brown, Eric S.; The atomic battery; Technology Review: Published by MIT; 4 pgs.; Jun. 16, 2005.
Carroll et al.; U.S. Appl. No. 13/956,946 entitled "Biostimulator Circuit with Flying Cell," filed Aug. 1, 2013.
Decision to grant a European patent of the European Patent Office dated Oct. 12, 2017 for related European Patent Application No. 16173491.8.
Decision to grant a European patent of the European Patent Office dated Oct. 13, 2016 for related European Patent Application No. 11848333.8.
European Office Action of the European Patent Office dated Oct. 21, 2015 for related European Patent Application No. 11848333.8.
European search report of the European Patent Office dated Jul. 26, 2016 for related European Patent Application No. 16173491.8.
Examiner Initiated Interview Summary dated Jul. 27, 2015; Related U.S. Appl. No. 13/324,802.
Intention to Grant of the European Patent Office dated Apr. 11, 2016 for related European Patent Application No. 11848333.8.
Intention to Grant of the European Patent Office dated Apr. 11, 2016 for related European Patent Application No. 16173491.8.
International Preliminary Report on Patentability of the International Searching Authority dated Jun. 27, 2013 for Yelated PCT Application No. PCT/US11/64671.
International Search Report and Written Opinion of the International Searching Authority dated Apr. 5, 2012 for related PCT Application No. PCT/US11/64671.
Imich et al.; Do we need pacemakers resistant to magnetic resonance imaging; Europace; vol. 7; pp. 353-365; Feb. 2005.
Imich; Electronic security systems and active implantable medical devices; Journal of PACE; vol. 25; No. 8; pp. 1235-1258; Aug. 2002.
Jacobson et al.; U.S. Appl. No. 13/277,151 entitled "Leadless cardiac pacemaker with conducted communication," filed Oct. 19, 2011.
Jacobson, P.; U.S. Appl. No. 13/866,803 entitled "Leadless cardiac pacemaker system for usage in combination with an implantable cardioverter-defribrillator," filed Apr. 19, 2013.
Jacobson, Peter M.; U.S. Appl. No. 13/708,732 entitled "Leadless Cardiac Pacemaker Triggered by Conductive Communication," filed Dec. 7, 2012.
Khairkhahan et al.; U.S. Appl. No. 13/272,074 entitled "Delivery catheter systems and methods," filed Oct. 12, 2011.
Khairkhahan et al.; U.S. Appl. No. 13/272,082 entitled "Leadless cardiac pacemaker with anti-unscrewing feature," filed Oct. 12, 2011.
Khairkhahan et al.; U.S. Appl. No. 13/324,781 entitled "Delivery Catheter Systems and Methods," filed Dec. 13, 2011.
Khairkhahan et al.; U.S. Appl. No. 13/331,922 entitled "Leadless Pacemaker with Radial Fixation Mechanism," filed Dec. 20, 2011.
Luchinger; Safety aspects of cardiac pacemakers in magnetic resonance imaging; Dissertation submitted to the Swiss Federal Institute of Technology Zurich; 137 pages; 2002 (month unavailable).
Luechinger et al.; Force and torque effects of a 1.5-tesla MRI scanner of cardiac pacemakers and ICDs; Journal of PACE; vol. 24; No. 2; pp. 199-205; Feb. 2001.
Luechinger et al.; In vivo heating of pacemaker leads during magnetic resonance imaging; European Heart Journal vol. 26; pp. 376-383; Feb. 2005.
Non-Final Office Action dated Jan. 21, 2015; Related U.S. Appl. No. 13/324,802.
Notice of Allowance dated Jul. 27, 2015; related U.S. Appl. No. 13/324,802.
Nyenhuis et al.; MRI and Implanted Medical Devices: Basic Interactions with an emphasis on heating; vol. 5; No. 3 pp. 467-480; Sep. 2005.
Ostroff et al.; U.S. Appl. No. 13/910,896 entitled "Leadless Pacemaker with Multiple Electrodes," filed Jun. 5, 2013.
Ostroff, Alan; U.S. Appl. No. 13/272,092 entitled "Temperature sensor for a leadless cardiac pacemaker," filed Oct. 12, 2011.
Ostroff, Alan; U.S. Appl. No. 13/915,560 entitled "MRI Compatible Leadless Cardiac Pacemaker," filed Jun. 11, 2013.
Ostroff, Alan; U.S. Appl. No. 13/967,180 entitled "Leadless Cardiac Pacemaker with Secondary Fixation Capability", filed Aug. 14, 2013.
Pertijs et al.; U.S. Appl. No. 13/901,414 entitled "Temperature Sensor for a Leadless Cardiac Pacemaker," filed May 23, 2013.
Response to Restriction Requirement Filed May 22, 2104; Related U.S. Appl. No. 13/324,802.
Restriction Requirement dated May 1, 2014; Related U.S. Appl. No. 13/324,802.
Shellock et al.; Cardiac pacemaker: In vitro assessment at 1.5 T; Am Heart J; vol. 151; No. 2; pp. 436-443; Feb. 2006.
Supplementary European search report of the European Patent Office dated Apr. 17, 2014 for related European Patent Application No. 11848333.8.
U.S. Appl. No. 10/891,747 entitled "System and method for synchronizing supplemental pacing pulses generated by a satellite pacing device with primary pulses delivered by a separate pacing device," filed Jul. 14, 2004 (abandoned prior to pub.: CIP of this app. is U.S. Pat. No. 7,630,767).
Varady et al.; U.S. Appl. No. 13/669,242 entitled "Leadless Cardiac Pacemaker with Integral Battery and Redundant Welds," filed Nov. 5, 2012.

* cited by examiner

Fig. 7A
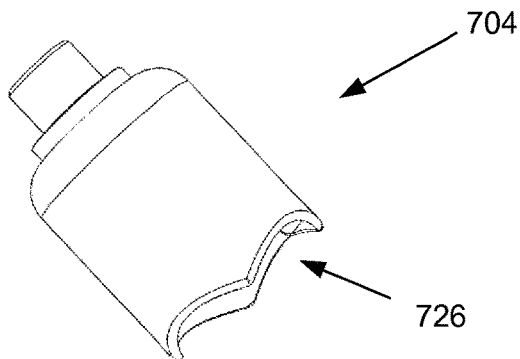
Fig. 7B
Fig. 7C
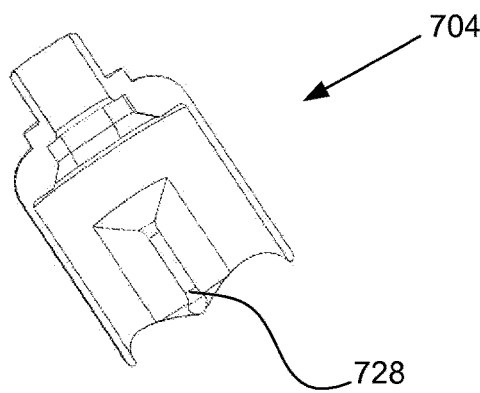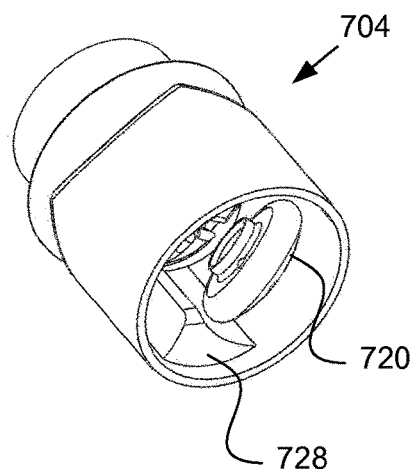
Fig. 7D
Fig. 7E
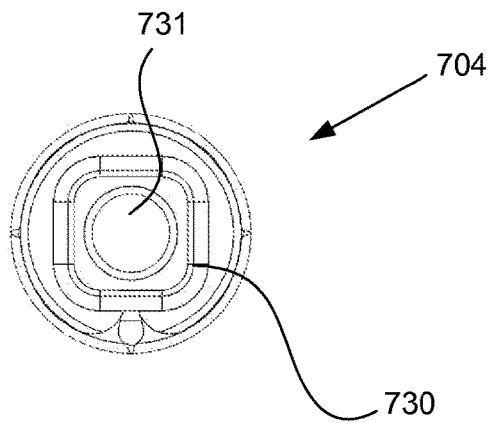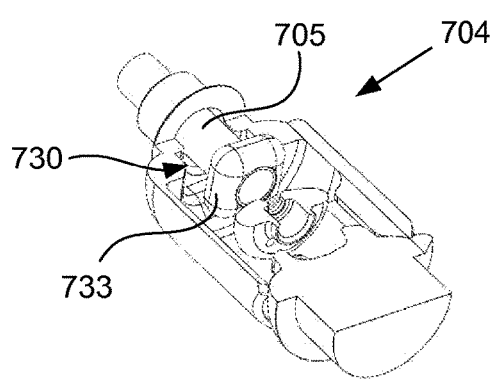

PACEMAKER RETRIEVAL SYSTEMS AND METHODS

CROSS REFERENCE TO RELATED APPLICATIONS

The present application is a Continuation application of co-pending U.S. patent application Ser. No. 16/214,709, filed Dec. 10, 2018, which is a Continuation application of U.S. patent application Ser. No. 14/816,302, filed Aug. 3, 2015, now issued as U.S. Pat. No. 10,188,425, entitled "Pacemaker Retrieval Systems and Methods," which is a Continuation application of U.S. patent application Ser. No. 13/324,802, filed Dec. 13, 2011, now issued as U.S. Pat. No. 9,126,032, entitled "Pacemaker Retrieval Systems and Methods," which claims the benefit of U.S. Provisional Patent Application No. 61/422,622, filed Dec. 13, 2010, titled "Pacemaker Retrieval Systems and Methods", each of which is incorporated herein by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure relates to leadless cardiac pacemakers, and more particularly, to features and methods by which they are removed from the heart. More specifically, the present disclosure relates to features and methods for retrieving a leadless cardiac pacemaker from tissue.

BACKGROUND

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. Pulse generator parameters are usually interrogated and modified by a programming device outside the body, via a loosely-coupled transformer with one inductance within the body and another outside, or via electromagnetic radiation with one antenna within the body and another outside. The generator usually connects to the proximal end of one or more implanted leads, the distal end of which contains one or more electrodes for positioning adjacent to the inside or outside wall of a cardiac chamber. The leads have an insulated electrical conductor or conductors for connecting the pulse generator to electrodes in the heart. Such electrode leads typically have lengths of 50 to 70 centimeters.

Although more than one hundred thousand conventional cardiac pacing systems are implanted annually, various well-known difficulties exist, of which a few will be cited. For example, a pulse generator, when located subcutaneously, presents a bulge in the skin that patients can find unsightly, unpleasant, or irritating, and which patients can subconsciously or obsessively manipulate or "twiddle". Even without persistent manipulation, subcutaneous pulse generators can exhibit erosion, extrusion, infection, and disconnection, insulation damage, or conductor breakage at the wire leads. Although sub-muscular or abdominal placement can address some concerns, such placement involves a more difficult surgical procedure for implantation and adjustment, which can prolong patient recovery.

A conventional pulse generator, whether pectoral or abdominal, has an interface for connection to and disconnection from the electrode leads that carry signals to and from the heart. Usually at least one male connector molding has at least one terminal pin at the proximal end of the electrode lead. The male connector mates with a corresponding female connector molding and terminal block within the connector molding at the pulse generator. Usually a setscrew is threaded in at least one terminal block per electrode lead to secure the connection electrically and mechanically. One or more O-rings usually are also supplied to help maintain electrical isolation between the connector moldings. A setscrew cap or slotted cover is typically included to provide electrical insulation of the setscrew. This briefly described complex connection between connectors and leads provides multiple opportunities for malfunction.

Other problematic aspects of conventional pacemakers relate to the separately implanted pulse generator and the pacing leads. By way of another example, the pacing leads, in particular, can become a site of infection and morbidity. Many of the issues associated with conventional pacemakers are resolved by the development of a self-contained and self-sustainable pacemaker, or so-called leadless pacemaker, as described in the related applications cited above.

Self-contained or leadless pacemakers or other biostimulators are typically fixed to an intracardial implant site by an actively engaging mechanism such as a screw or helical member that screws into the myocardium.

SUMMARY OF THE DISCLOSURE

A catheter for retrieving a medical device from a patient is provided comprising, a handle, a catheter shaft coupled to the handle, a snare disposed within the catheter shaft and extendable distally beyond the catheter shaft, a docking cap disposed on a distal portion of the catheter shaft, the docking cap being rotatable independent of the catheter shaft, and a torque shaft disposed within the catheter shaft and selectively connectable to the docking cap, the torque shaft configured to rotate within the catheter shaft to apply rotational torque to the docking cap when connected to the docking cap.

In some embodiments, the catheter further comprises an interference feature disposed on an interior surface of the docking cap, the interference feature configured to engage a corresponding interference feature on the medical device to be retrieved. In some embodiments, the interference feature comprises a ridge.

In some embodiments, the catheter further comprises slot disposed inside the docking cap, the slot configured to engage a key on the torque shaft. In one embodiment, the torque shaft is configured to apply rotational torque to the docking cap when the docking cap slot is engaged with the key on the torque shaft.

In another embodiment, a proximal portion of the torque shaft is coupled to a control knob on the handle. In some embodiments, longitudinal movement of the torque knob along the handle causes the torque shaft to engage or disengage the slot in the docking cap. In another embodiment, rotation of the control knob causes the torque shaft and docking cap to rotate when the key on the torque shaft is engaged with the docking cap slot. In yet another embodiment, longitudinal movement of the control knob along the handle moves the torque shaft and snare longitudinally.

In some embodiments of the catheter, the snare comprises a plurality of loops. In other embodiments, the snare comprises a single loop. In one embodiment, the single loop comprises a loop perpendicular to the catheter shaft. In other embodiments, the snare is offset from a longitudinal axis of the catheter when the snare is advanced distally beyond the catheter shaft.

A leadless pacemaker and retrieval system is provided, comprising a leadless cardiac pacemaker having a retrieval feature coupled to the pacemaker with at least one flexible stem, and a delivery catheter comprising a handle, a catheter shaft coupled to the handle, a snare disposed within the catheter shaft and extendable distally beyond the catheter shaft, a docking cap disposed on a distal portion of the catheter shaft, the docking cap being rotatable independent of the catheter shaft and being sized and configured to receive the retrieval feature of the leadless cardiac pacemaker, and a torque shaft disposed within the catheter shaft and selectively connectable to the docking cap, the torque shaft configured to rotate within the catheter shaft to apply rotational torque to the docking cap when connected to the docking cap, and to apply rotational torque to the leadless cardiac pacemaker when the pacemaker is disposed in the docking cap.

In some embodiments, the catheter further comprises an interference feature disposed on an interior surface of the docking cap, the interference feature configured to engage a corresponding interference feature on the pacemaker. In some embodiments, the interference feature comprises a ridge.

In some embodiments, the catheter further comprises slot disposed inside the docking cap, the slot configured to engage a key on the torque shaft. In one embodiment, the torque shaft is configured to apply rotational torque to the docking cap when the docking cap slot is engaged with the key on the torque shaft.

In another embodiment, a proximal portion of the torque shaft is coupled to a control knob on the handle. In some embodiments, longitudinal movement of the torque knob along the handle causes the torque shaft to engage or disengage the slot in the docking cap. In another embodiment, rotation of the control knob causes the torque shaft and docking cap to rotate when the key on the torque shaft is engaged with the docking cap slot. In yet another embodiment, longitudinal movement of the control knob along the handle moves the torque shaft and snare longitudinally.

In some embodiments of the catheter, the snare comprises a plurality of loops. In other embodiments, the snare comprises a single loop. In one embodiment, the single loop comprises a loop perpendicular to the catheter shaft. In other embodiments, the snare is offset from a longitudinal axis of the catheter when the snare is advanced distally beyond the catheter shaft.

A method of retrieving a medical device from a patient is also provided, comprising positioning a snare of a catheter in proximity to a retrieval feature of the medical device, grasping the retrieval feature of the medical device with the snare, pulling the snare proximally into the catheter to position the retrieval feature of the medical device inside a docking cap of the catheter, and applying rotational torque from the docking cap to the medical device to unscrew the medical device from tissue in the patient.

In some embodiments, the medical device comprises a leadless cardiac pacemaker.

In one embodiment, the applying rotational torque step further comprises rotating a torque shaft coupled to the docking cap. In another embodiment, the applying rotational torque step further comprises engaging a key feature on the torque shaft with a matching slot in the docking cap.

In some embodiments, the method further comprises covering the medical device with a protective sheath and removing the device from the patient.

In some embodiments, the grasping step further comprises grasping the retrieval feature with a loop of the snare. In other embodiments, the grasping step further comprises advancing a snare sleeve distally over the snare to collapse the snare.

BRIEF DESCRIPTION OF THE DRAWINGS

FIGS. 7A-7E illustrate several embodiments of a docking cap of a retrieval catheter system.

DETAILED DESCRIPTION

Figure 1:
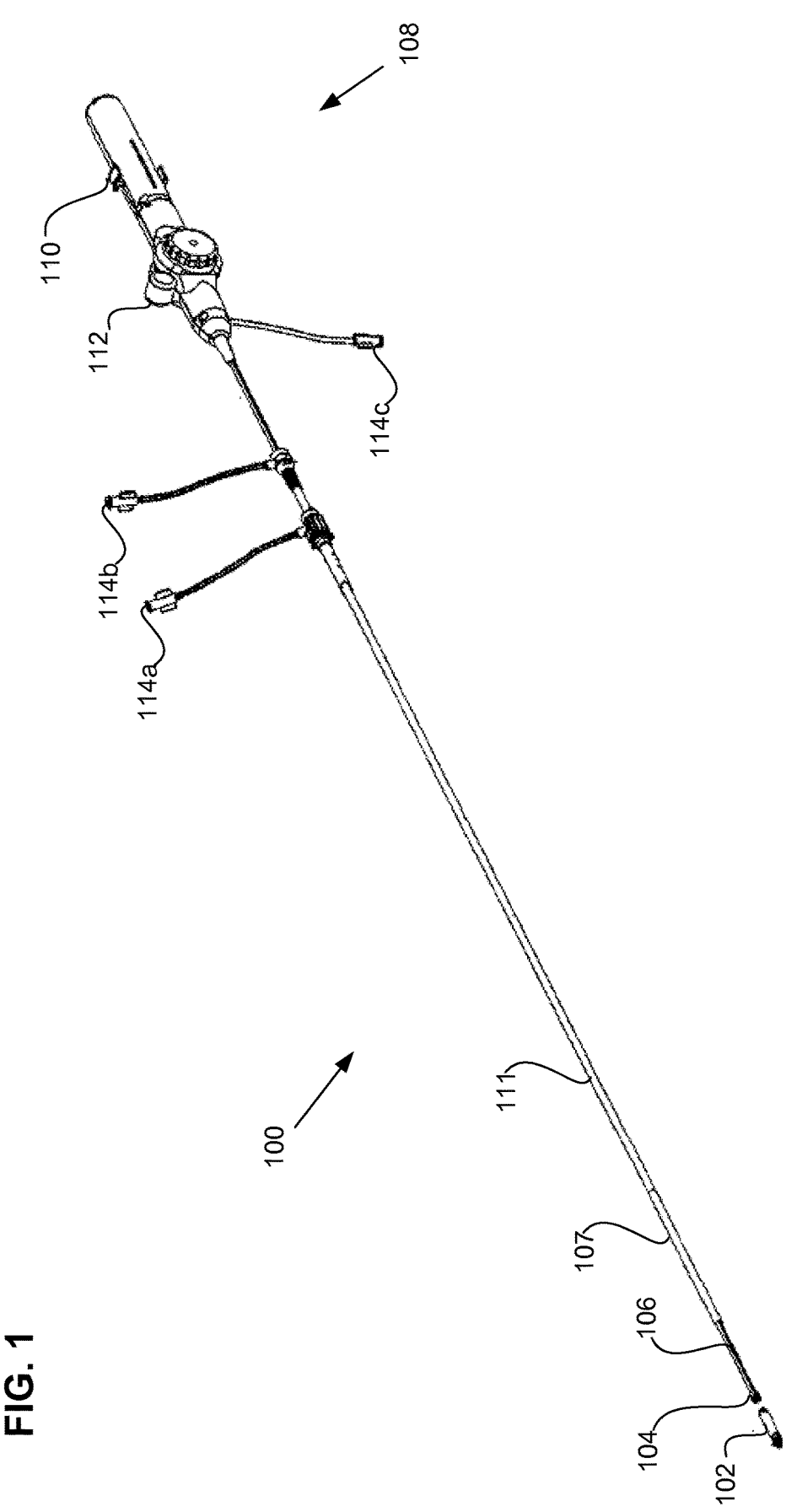
FIG. 1 illustrates one embodiment of a pacemaker retrieval catheter system.

Various embodiments for delivering system comprising one or more leadless cardiac pacemakers or biostimulators are described. A leadless cardiac pacemaker can communicate by conducted communication, representing a substantial departure from conventional pacing systems. For example, an illustrative cardiac pacing system can perform cardiac pacing that has many of the advantages of conventional cardiac pacemakers while extending performance, functionality, and operating characteristics with one or more of several improvements.

In some embodiments of a cardiac pacing system, cardiac pacing is provided without a pulse generator located in the pectoral region or abdomen, without an electrode-lead separate from the pulse generator, without a communication coil or antenna, and without an additional requirement on battery power for transmitted communication.

An embodiment of a cardiac pacing system configured to attain these characteristics comprises a leadless cardiac pacemaker that is substantially enclosed in a hermetic housing suitable for placement on or attachment to the inside or outside of a cardiac chamber. The pacemaker can have two or more electrodes located within, on, or near the housing, for delivering pacing pulses to muscle of the cardiac chamber and optionally for sensing electrical activity from the muscle, and for bidirectional communication with at least one other device within or outside the body. The housing can contain a primary battery to provide power for pacing, sensing, and communication, for example bidirectional communication. The housing can optionally contain circuits for sensing cardiac activity from the electrodes. The housing contains circuits for receiving information from at least one other device via the electrodes and contains circuits for generating pacing pulses for delivery via the electrodes. The housing can optionally contain circuits for transmitting information to at least one other device via the electrodes and can optionally contain circuits for monitoring device health. The housing contains circuits for controlling these operations in a predetermined manner.

In some embodiments, a cardiac pacemaker can be adapted for delivery and implantation into tissue in the human body. In a particular embodiment, a leadless cardiac pacemaker can be adapted for implantation adjacent to heart tissue on the inside or outside wall of a cardiac chamber, using two or more electrodes located on or within the housing of the pacemaker, for pacing the cardiac chamber upon receiving a triggering signal from at least one other device within the body.

Self-contained or leadless pacemakers or other biostimulators are typically fixed to an intracardial implant site by an actively engaging mechanism or primary fixation mechanism such as a screw or helical member that screws into the myocardium. Examples of such leadless biostimulators are described in the following publications, the disclosures of which are incorporated by reference: (1) U.S. application Ser. No. 11/549,599, filed on Oct. 13, 2006, entitled "Leadless Cardiac Pacemaker System for Usage in Combination with an Implantable Cardioverter-Defibrillator", and published as US2007/0088394A1 on Apr. 19, 2007; (2) U.S. application Ser. No. 11/549,581 filed on Oct. 13, 2006, entitled "Leadless Cardiac Pacemaker", and published as US2007/0088396A1 on Apr. 19, 2007; (3) U.S. application Ser. No. 11/549,591, filed on Oct. 13, 2006, entitled "Leadless Cardiac Pacemaker System with Conductive Communication" and published as US2007/0088397A1 on Apr. 19, 2007; (4) U.S. application Ser. No. 11/549,596 filed on Oct. 13, 2006, entitled "Leadless Cardiac Pacemaker Triggered by Conductive Communication" and published as US2007/0088398A1 on Apr. 19, 2007; (5) U.S. application Ser. No. 11/549,603 filed on Oct. 13, 2006, entitled "Rate Responsive Leadless Cardiac Pacemaker" and published as US2007/0088400A1 on Apr. 19, 2007; (6) U.S. application Ser. No. 11/549,605 filed on Oct. 13, 2006, entitled "Programmer for Biostimulator System" and published as US2007/0088405A1 on Apr. 19, 2007; (7) U.S. application Ser. No. 11/549,574, filed on Oct. 13, 2006, entitled "Delivery System for Implantable Biostimulator" and published as US2007/0088418A1 on Apr. 19, 2007; and (8) International Application No. PCT/US2006/040564, filed on Oct. 13, 2006, entitled "Leadless Cardiac Pacemaker and System" and published as WO07047681A2 on Apr. 26, 2007.

In addition to the primary fixation mechanism, such as a helix, some pacemakers may further include a secondary fixation mechanism to provide another feature for keeping the biostimulator in place within the body. Secondary fixation mechanisms can be either active (e.g., the secondary fixation mechanism can actively engage tissue, either within or outside the heart), or can be passive (e.g., the secondary fixation mechanism is not attached to tissue but rather prevents the biostimulator from moving around in the body in the case of accidental detachment). Further details on secondary fixation mechanisms can be found in U.S. application Ser. No. 12/698,969.

Self-contained or leadless pacemakers or other biostimulators are typically fixed to an intracardial implant site by an actively engaging mechanism such as a screw or helical member that screws into the myocardium. In case of malfunction, it is highly desirable to be able to retrieve the leadless pacemaker of biostimulators both acutely (during the implantation procedure) or chronically, after a period of time post implantation minimally invasively.

FIG. 1 illustrates a pacemaker retrieval catheter 100 configured for retrieval of a leadless pacemaker 102 from a patient. More specifically, the catheter 100 is configured to remove a leadless cardiac pacemaker from the heart of a patient. The retrieval catheter 100 can include docking cap 104, catheter shaft 106, protective sheath 107, handle 108, snare slider 110, guide catheter shaft 111, deflection arm 112, and flush ports 114*a*, 114*b*, and 114*c*.

The leadless cardiac pacemaker 102 can be, for example, similar to the pacemakers described above in the referenced applications. The catheter shaft can be made from braided shaft (e.g. pebax with stainless steel braid) and can include segments with different stiffness's throughout the shaft. The deflection knob 112 can be used to steer and guide the catheter during removal of the pacemaker. Snare slider 110 can be configured to control operation of the snare for capturing a leadless cardiac pacemaker, and will be described in more detail below. The flush ports 114*a*, 114*b*, and 114*c* can be used to flush saline or other fluids through the catheter, guide catheter and pacemaker capture sheath.

Sheath 107 can be advanced longitudinally over catheter shaft 106 and guide catheter shaft 111 to cover the pacemaker during retrieval and prevent the pacemaker from catching onto or damaging tissue. In some embodiments, the sleeve can include a radio-opaque coating, such as barium sulfate, or alternatively, can include a platinum or metal feature at the distal end of the sleeve, so that under visualization a user can determine when the sleeve is fully covering the pacemaker prior to removal.

Figure 2A:
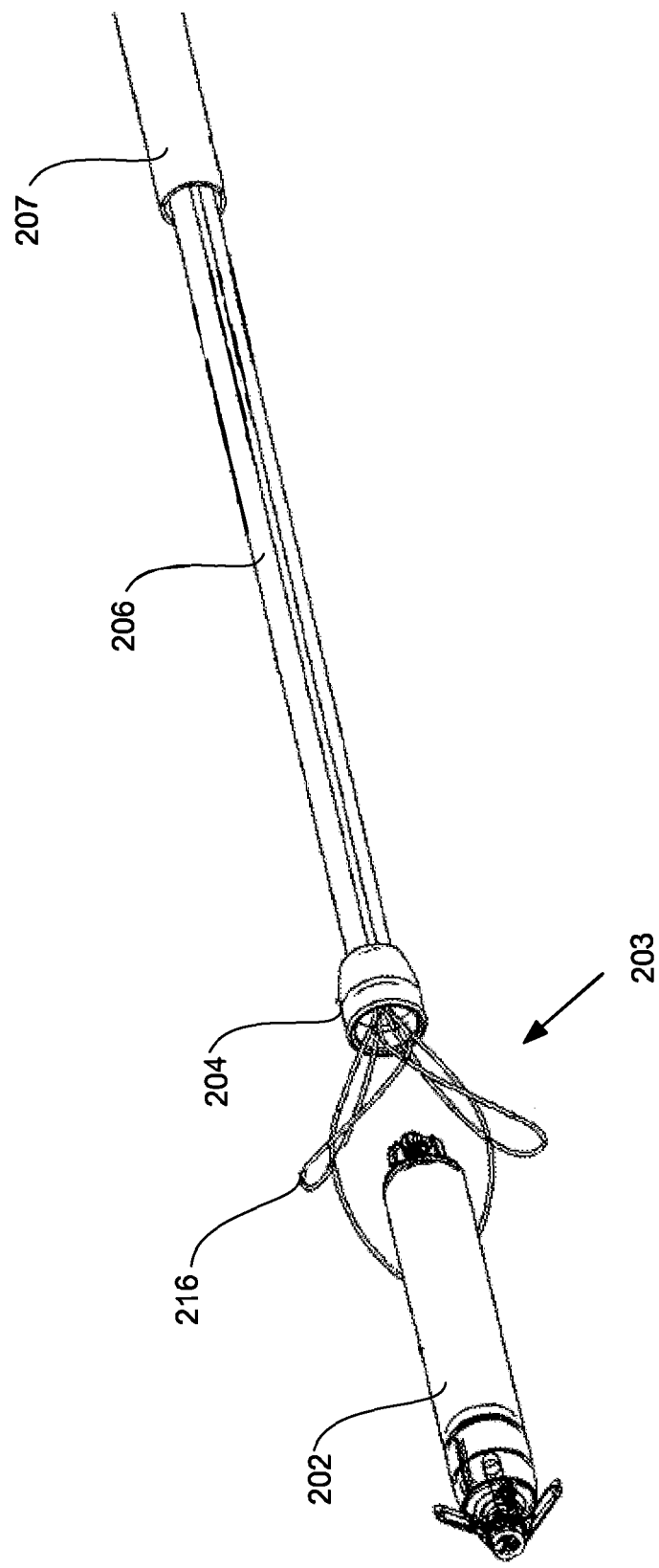
FIGS. 2A-2C show various close-up views of a distal portion of a retrieval catheter system.

FIG. 2A illustrates a close-up view of one embodiment of a distal portion of the pacemaker retrieval catheter 100 shown in FIG. 1. The distal portion of the retrieval catheter can include snare 203 configured to grasp a leadless cardiac pacemaker or other medical device, and docking cap 204 configured to allow docking of the leadless pacemaker with the retrieval catheter after engaging the pacemaker with the snare. FIG. 2A also illustrates catheter shaft 206 terminating at the docking cap 204, and protective sheath 207 positioned along the shaft slightly proximal to the docking cap and leadless pacemaker.

As shown in FIG. 2A, the snare 203 can comprise at least one loop 216 extending from the catheter shaft. As the snare is advanced distally out of the retrieval system from docking cap 204, the loops can expand in size to aid a user in positioning the snare around or in proximity to the pacemaker to be retrieved. In some embodiments, as in FIG. 2A, the snare can include multiple loops, such as three loops. However, any number of loops can be used as long as the catheter shaft contains sufficient volume to accommodate the loops.

Figure 2B:
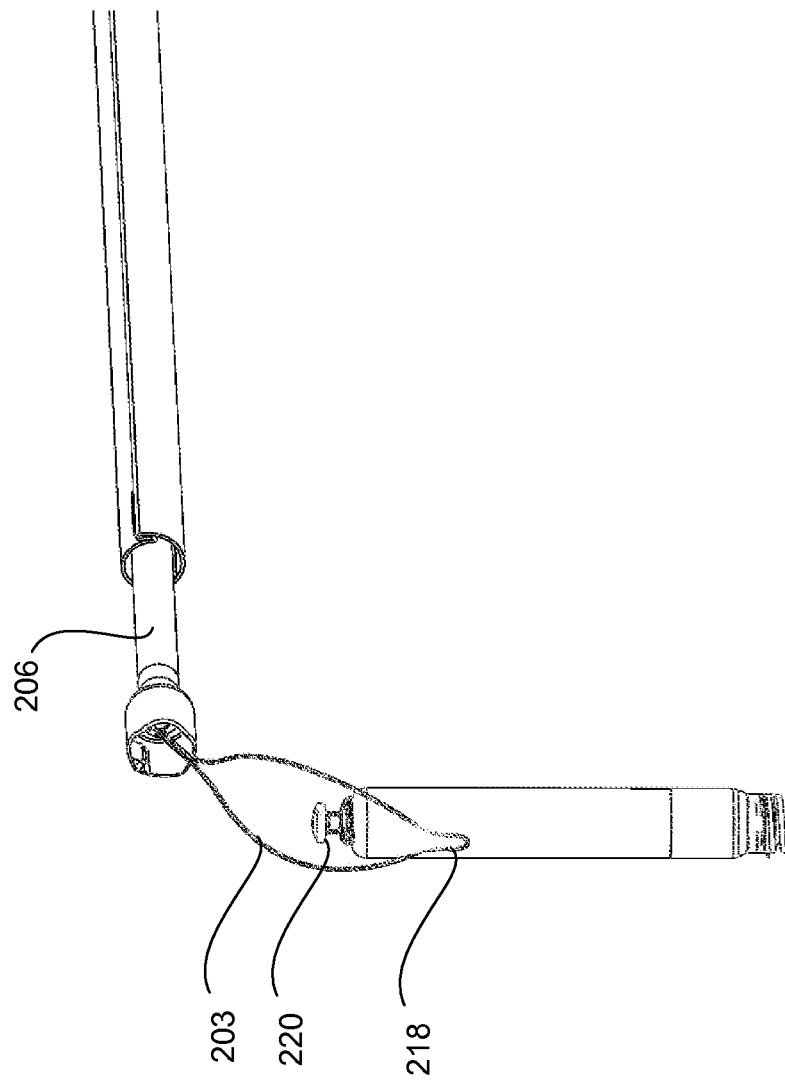

In another embodiment, as shown in FIG. 2B, the snare can include only a single loop. Also shown in FIG. 2B, the loops can include any number of features 218 to aid in grasping a pacemaker or medical device for retrieval. In FIG. 2B, the feature 218 can comprise, for example, a notch feature. In some embodiments, the loops of the snare can be positioned off axis from the center of the catheter shaft to aid in keeping the pacemaker in line with the catheter during removal. For example, in FIG. 2B, the single loop snare 203 can include a notch feature 218 and be positioned off axis from the longitudinal axis of the catheter shaft 206. Since the snare is off axis from the catheter, the snare can be looped around retrieval feature 220 of the pacemaker by positioning the catheter adjacent to the pacemaker and allowing the loop to come into contact with the housing of the pacemaker. As the catheter is pulled away from the pacemaker, the snare can slide up the pacemaker, and notch feature 218 can be allowed to engage the retrieval feature of the pacemaker.

Figure 2C:
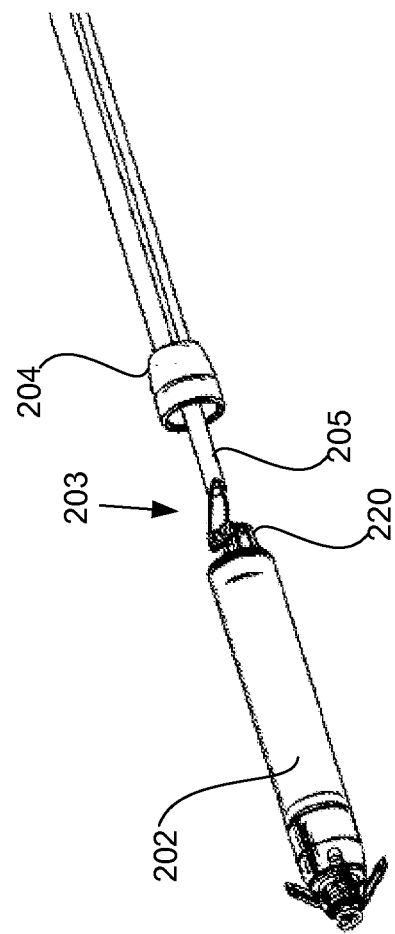

FIG. 2C illustrates the snare 203 grasping a retrieval feature 220 of the leadless cardiac pacemaker 202. In the illustrated embodiment, snare locking sleeve 205 can be advanced distally over the snare from docking cap 204 of the catheter. As the snare locking sleeve advances distally along the snare, it can cause the loops of the snare to reduce in size, thereby grasping or locking onto the retrieval feature 220 of the pacemaker. In some embodiments, the snare locking sleeve 205 can also comprise a torque shaft that runs through the length of the catheter. Details of the torque shaft will be described in more detail below, but generally the torque shaft can be rotated independently of the catheter shaft and coupled to the docking cap of the catheter to apply rotational torque to the docking cap, and thus, to a pacemaker or medical device to be retrieved. In embodiments where the snare includes a plurality of loops, it may be more likely that one of the loops will grasp the pacemaker than in embodiments where the snare comprises only a single loop.

Figure 3A:
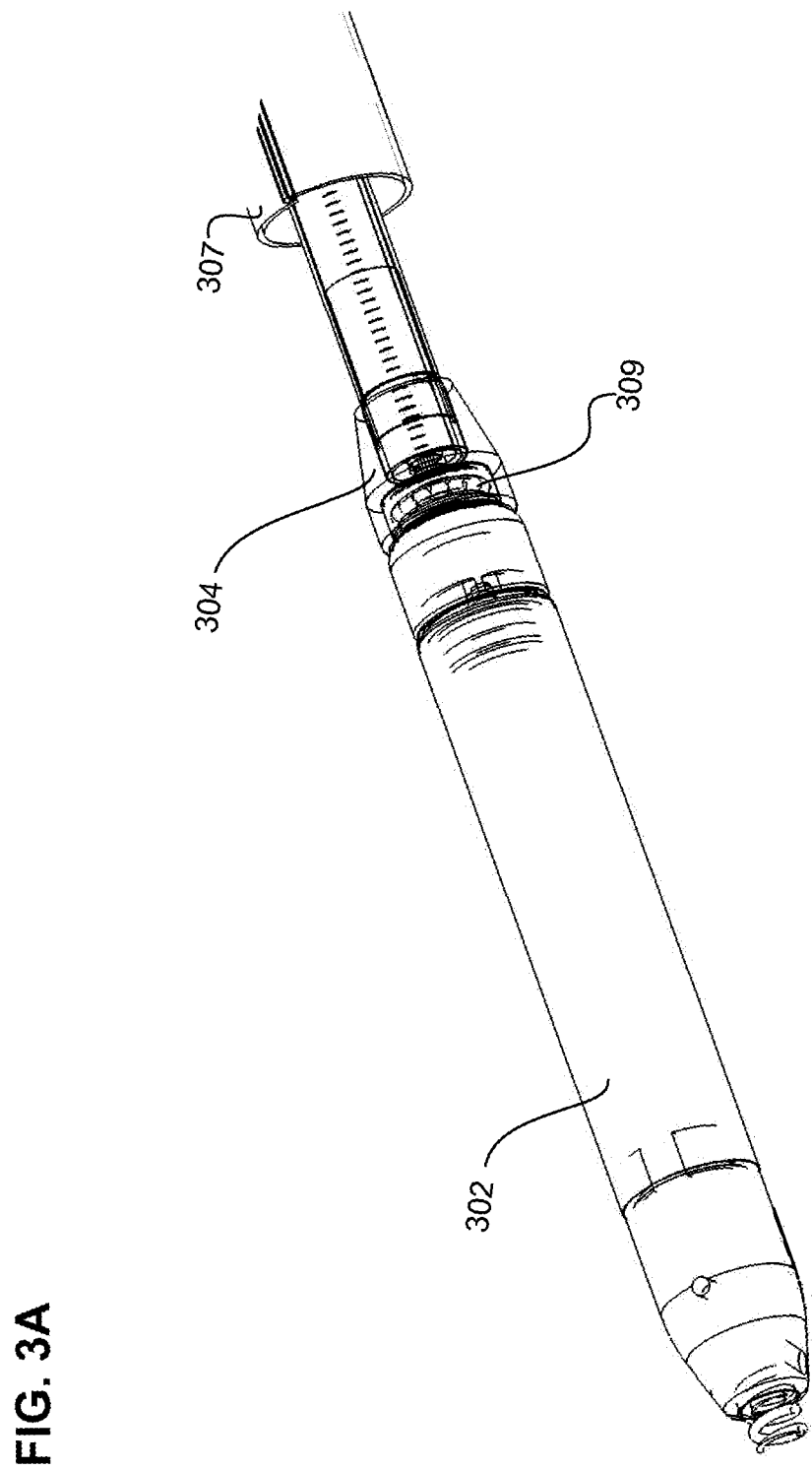
FIGS. 3A-3B illustrate a protective sheath of a retrieval catheter system.

FIG. 3A illustrates a close-up view of the distal portion of the retrieval catheter with the snare locked onto the retrieval feature (not shown) of the leadless pacemaker 302 and docked within docking cap 304. In some embodiments, as will be described in more detail below, the docking cap can include a key or interference feature configured to mate with and engage a corresponding key or feature on the pacemaker itself. In some embodiments, the key or slot on the docking cap can match a unique shape or feature of the retrieval feature of the pacemaker itself. Because the key or slot on or in the docking cap can mate with and engage the key or slot on the pacemaker, the retrieval catheter can be configured to apply torque to the pacemaker to unscrew and remove the pacemaker from tissue. FIG. 3A also illustrates protective sheath positioned slightly proximally to the docking cap 304 along the catheter shaft of the retrieval system.

As shown in FIG. 3A, the docking cap 304 can include ball bearings 309 which allow the docking cap to be free-rotating from the rest of the catheter shaft. This effectively reduces the removal torque and additional forces from the catheter body. The docking cap can be selectively coupled to a torque shaft (not shown) that extends through the length of the catheter to a torque knob on the handle (described below). When the torque shaft is coupled to the docking cap, rotation or actuation of the torque knob rotates the torque shaft, thereby rotating the docking cap 304 at the end of the retrieval catheter. In some embodiments, the docking cap can include a keyed portion or interference feature so as to apply additional torque to the pacemaker when unscrewing.

Figure 3B:
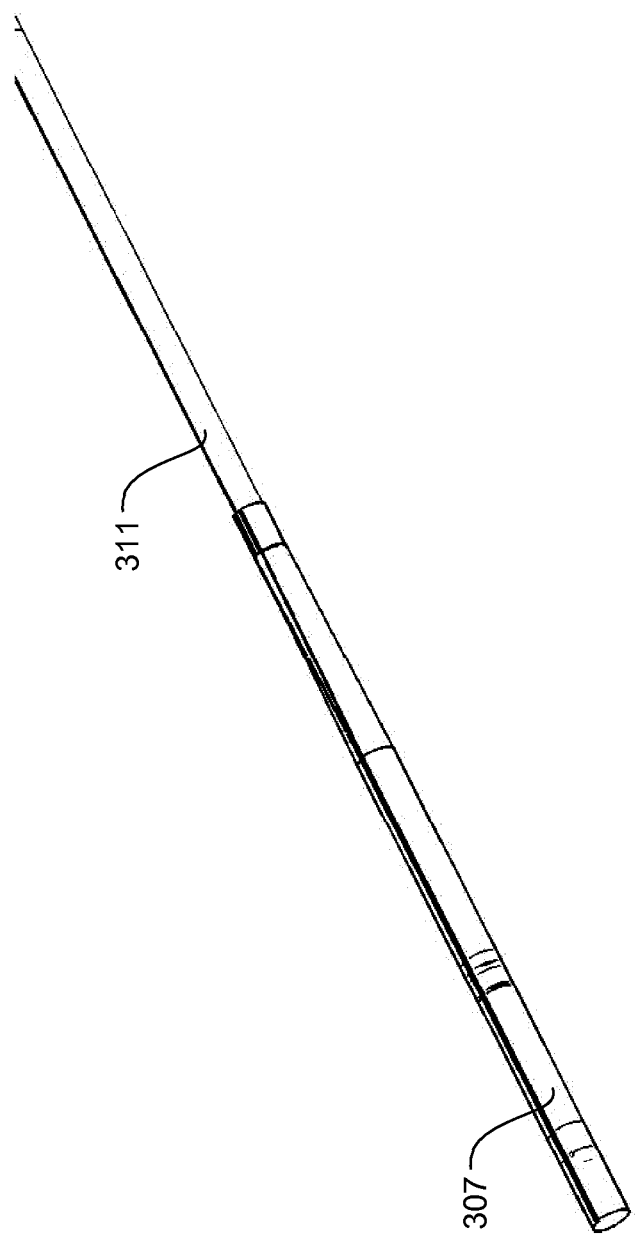

In FIG. 3B, the protective sheath 307 is shown disposed over the leadless cardiac pacemaker and positioned at the distal end of guide catheter shaft 311. As described above, the protective sheath can be configured to slide over the pacemaker to prevent any sharp edges or features of the pacemaker from tearing, damaging, or catching onto tissue during removal of the pacemaker. The protective sheath can be slidable along a longitudinal axis of the catheter so as to allow for covering and uncovering of the pacemaker with the sheath. In some embodiments, the protective sheath can include other form factors than illustrated in FIG. 3B. For example, in some retrieval scenarios where vegetative growth over the device is significant, the protective sheath may be of a larger diameter to accommodate the increase in size of the device.

The above description of FIGS. 1-3B can be used to illustrate one embodiment of a method of retrieving a medical device or leadless cardiac pacemaker from a patient. First, a retrieval catheter can be advanced into a patient until the docking cap of the catheter is in the vicinity of the pacemaker. Next, the snare of the retrieval catheter can be advanced distally outward from the catheter to surround the retrieval feature of the pacemaker. Once the snare is surrounding the retrieval feature of the pacemaker, the snare locking sleeve/torque shaft can be advanced distally along the snare to close the snare, causing the snare to grasp the retrieval feature of the pacemaker. Next, the snare and snare locking sleeve can be pulled proximally towards the docking cap of the catheter so as to engage the proximal end or retrieval feature of the pacemaker. Rotational torque can then be applied by the catheter to the pacemaker via the torque shaft and docking cap to unscrew the pacemaker from the tissue. The protective sheath can be advanced over the pacemaker, and the pacemaker can then be removed from the patient.

Figure 4:
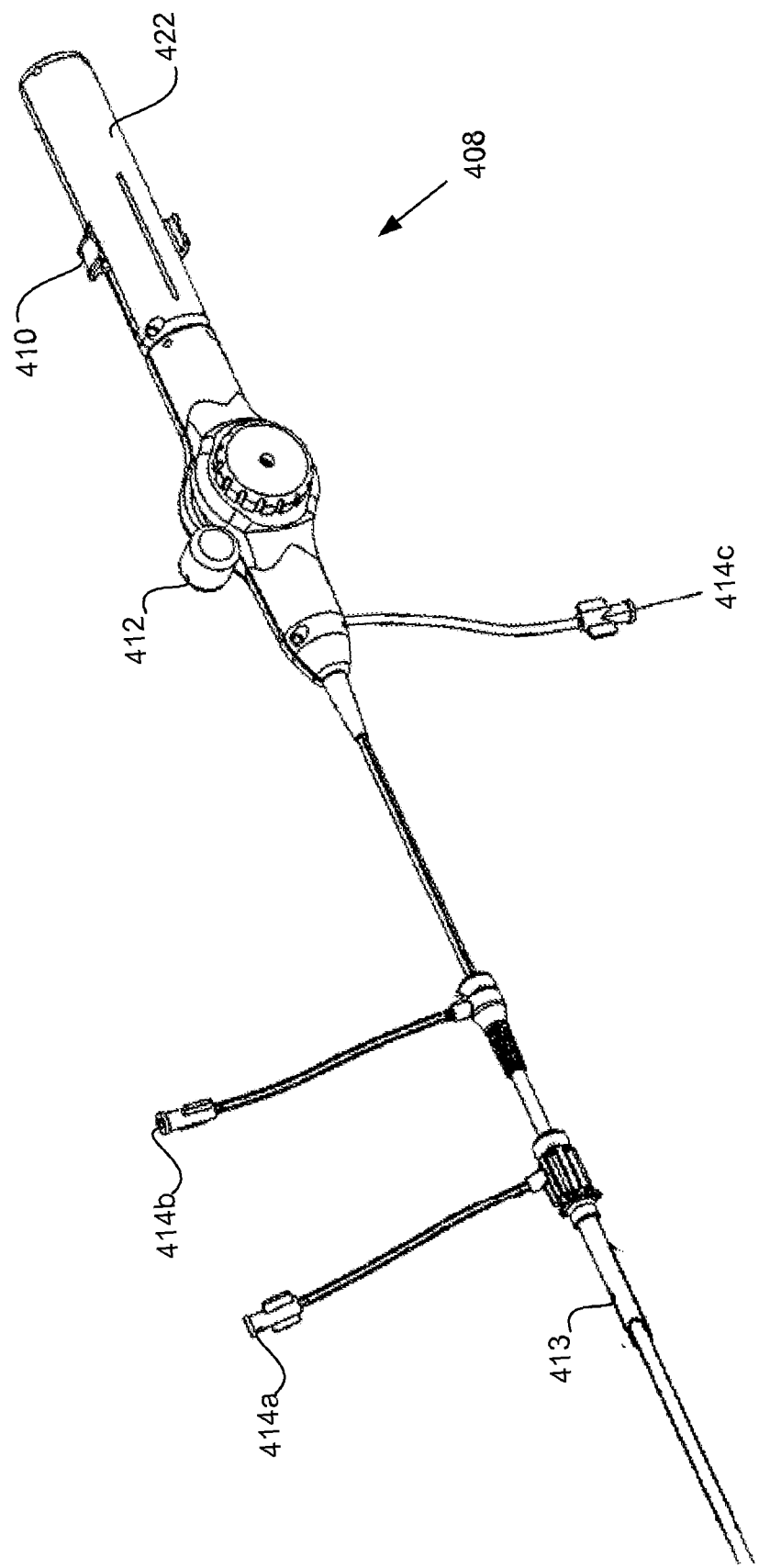
FIG. 4 shows a proximal portion of a retrieval catheter system including a handle.

FIG. 4 is a view of the proximal section of the retrieval catheter, showing pacemaker capture sheath 413, handle 408, snare slider 410, deflection arm 412, and flush ports 414a, 414b, and 414c. Deflection and steering of the distal portion of the catheter, including the portion of the catheter with the docking cap (shown above) can be achieved by manipulating the deflection arm 412 of handle 408. Opening and closing the loops of the snare (as illustrated in FIGS. 2A-2C) can be achieved by manipulating the snare slider 410 on the handle in the proximal and distal directions. Although the deflection arm and snare sliders are illustrated as mechanical features, it should be understood that various solutions can be used to steer the catheter and manipulate the snare. For example, the handle can include any number of mechanical features such as rotating knobs or sliding levers, or alternatively, can employ an electronic or hydraulic system with buttons and electric motors or hydraulic pistons. Once the pacemaker is snared and removed from within the heart of the patient (e.g., from within the right ventricle), the pacemaker can be pulled into the capture sheath 413. The capture sheath and pacemaker can then be withdrawn together from an introducer/trocar inserted in the patient (e.g., in the femoral vein). The capture sheath allows the pacemaker to cross a hemostatic seal provided by the introducer without damaging itself or the seal of the introducer.

A portion of the handle can comprise a torque knob 422 which controls rotation of the snare and/or docking cap of the retrieval catheter. The torque knob can be coupled to the docking cap via a torque shaft (not shown) that runs throughout the catheter shaft of the retrieval catheter. The torque knob can also be coupled to the snare, which runs also through the catheter shaft. Rotation of the torque knob clockwise or counter-clockwise can cause rotation of the torque shaft and thus, the docking cap. Longitudinal movement of the torque knob along the handle can slide the snare longitudinally within the catheter.

Figure 5A:
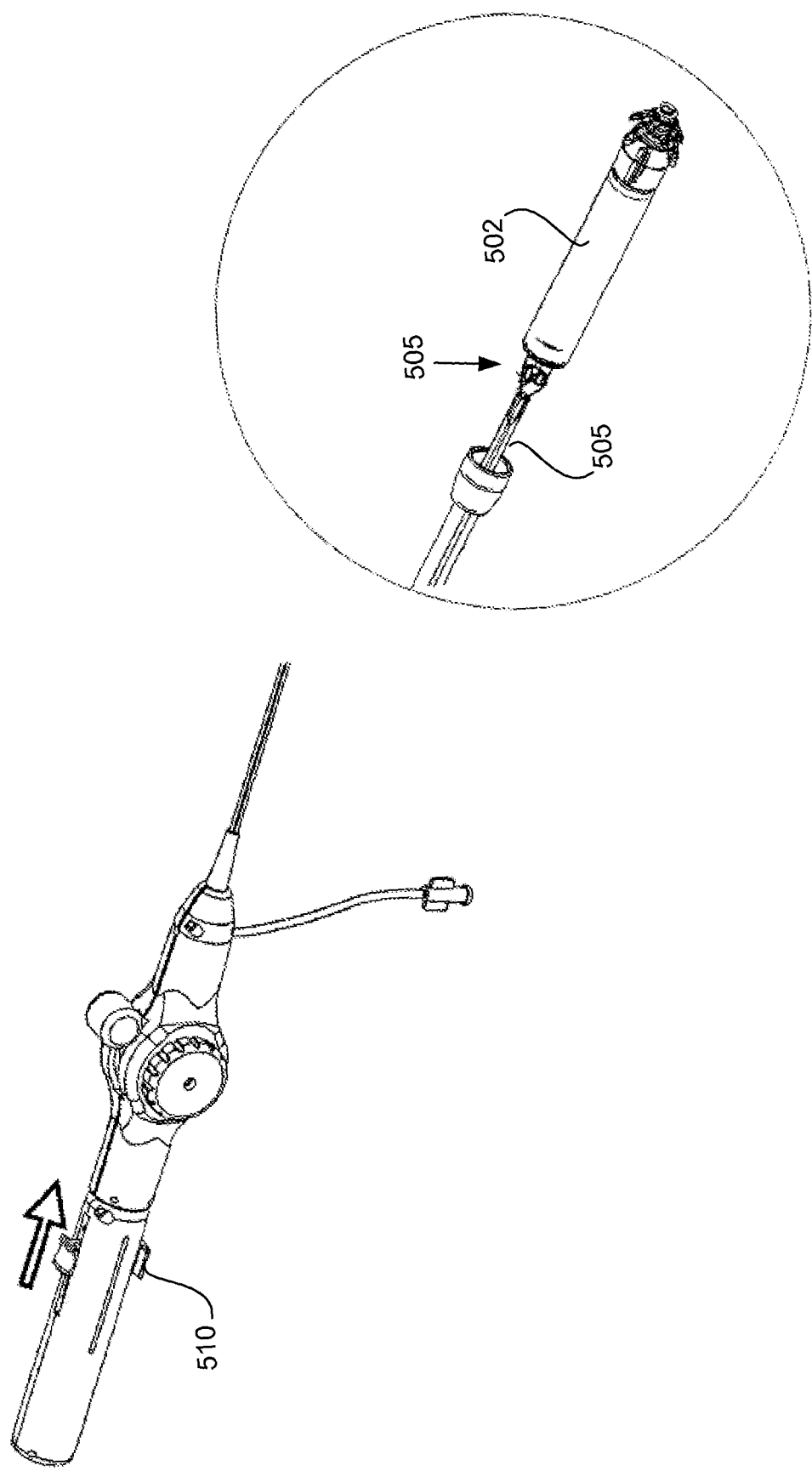
FIGS. 5A-5B illustrate operation of the handle of a retrieval catheter system.
Figure 5B:
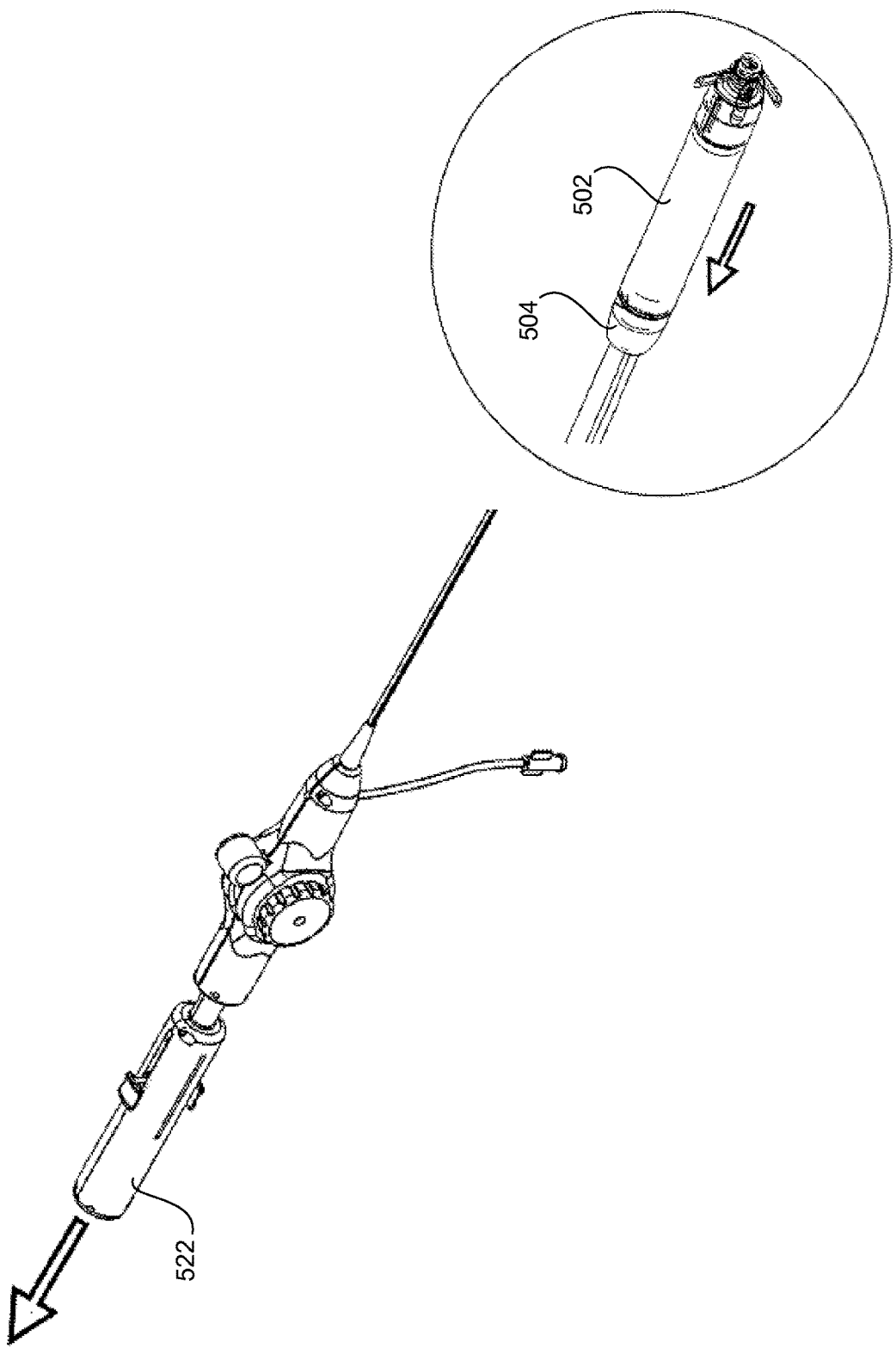

FIGS. 5A-5B illustrate how manipulation of the various features on the handle control the snare and snare locking sleeve on the distal portion of the catheter. In FIG. 5A, sliding snare slider 510 distally or forward can advance snare locking sleeve 505 over the snare, causing the snare to close around a retrieval feature of the pacemaker 502. As the locking sleeve advances over the snare, the diameter of the snare loop closes which locks the snare loop onto the retrieval feature of the pacemaker. Next, the torque knob 522 can be moved proximally, as shown in FIG. 5B, pulling the snare and snare locking sleeve proximally and causing the pacemaker 502 to come into contact with and dock within docking cap 504. In some embodiments, pulling the snare locking sleeve proximately can cause the snare to engage and become coupled with the docking cap. When the snare locking sleeve (also referred to as a torque shaft) is coupled to the docking cap, rotation of the torque sleeve causes the docking cap to rotate as well.

Figure 6A:
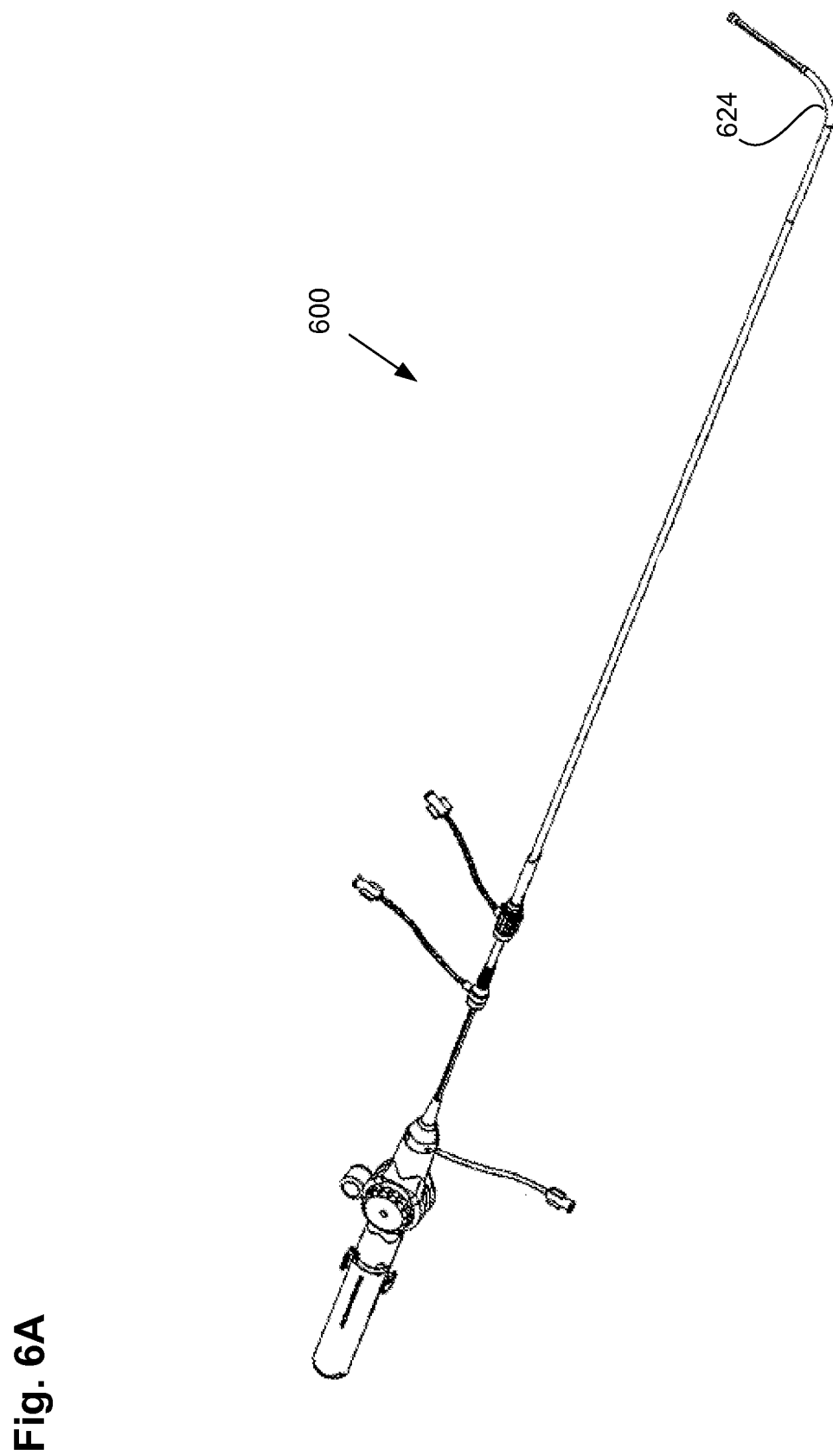
FIGS. 6A-6C show various embodiments of a retrieval catheter system including pre-bent curves in the catheter shaft.
Figure 6B:
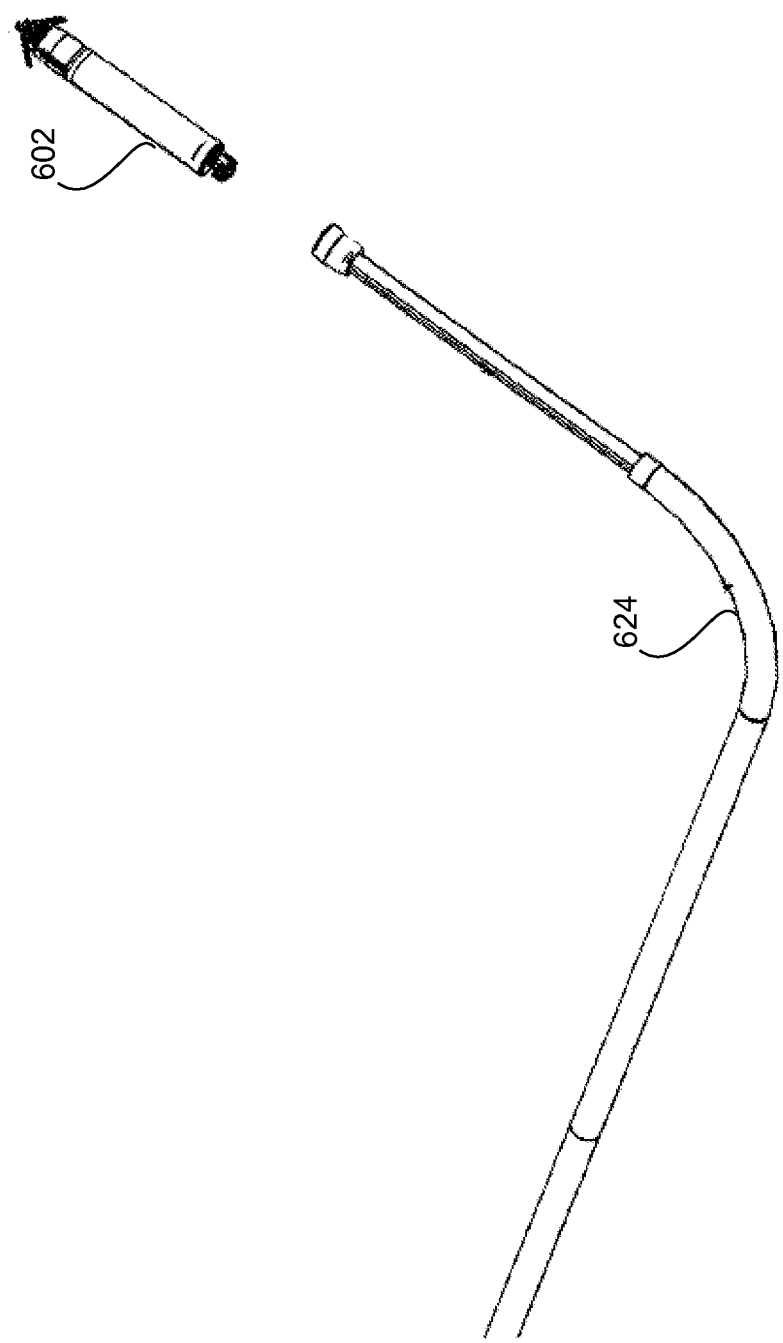

FIG. 6A illustrates one embodiment of a pacemaker retrieval catheter 600 having a pre-curved catheter shaft. The catheter may include a distal curve 624 to enhance steering and navigation of the retrieval catheter. In some embodiments, the distal curve can improve steering and navigation of the retrieval catheter by providing mechanical support that the tissue and vein structures may lack. In one embodiment of the retrieval system, the distal section of the guide catheter may be pre-curved to a 90 degree angle and 30 mm radius. The catheter may include a flush port on the proximal end to allow aspiration or irrigation of the guide catheter lumen. FIG. 6B is a close-up view of the distal section of the retrieval catheter with the snare retracted and showing the distal curve 624 of the catheter shaft. In some embodiments, the shaft can include a curve angle from 0-180 degrees and curve radius of 20-50 mm. FIG. 6B shows the retrieval catheter in the vicinity of the pacemaker 602, with the snare retracted into the catheter.

Figure 6C:
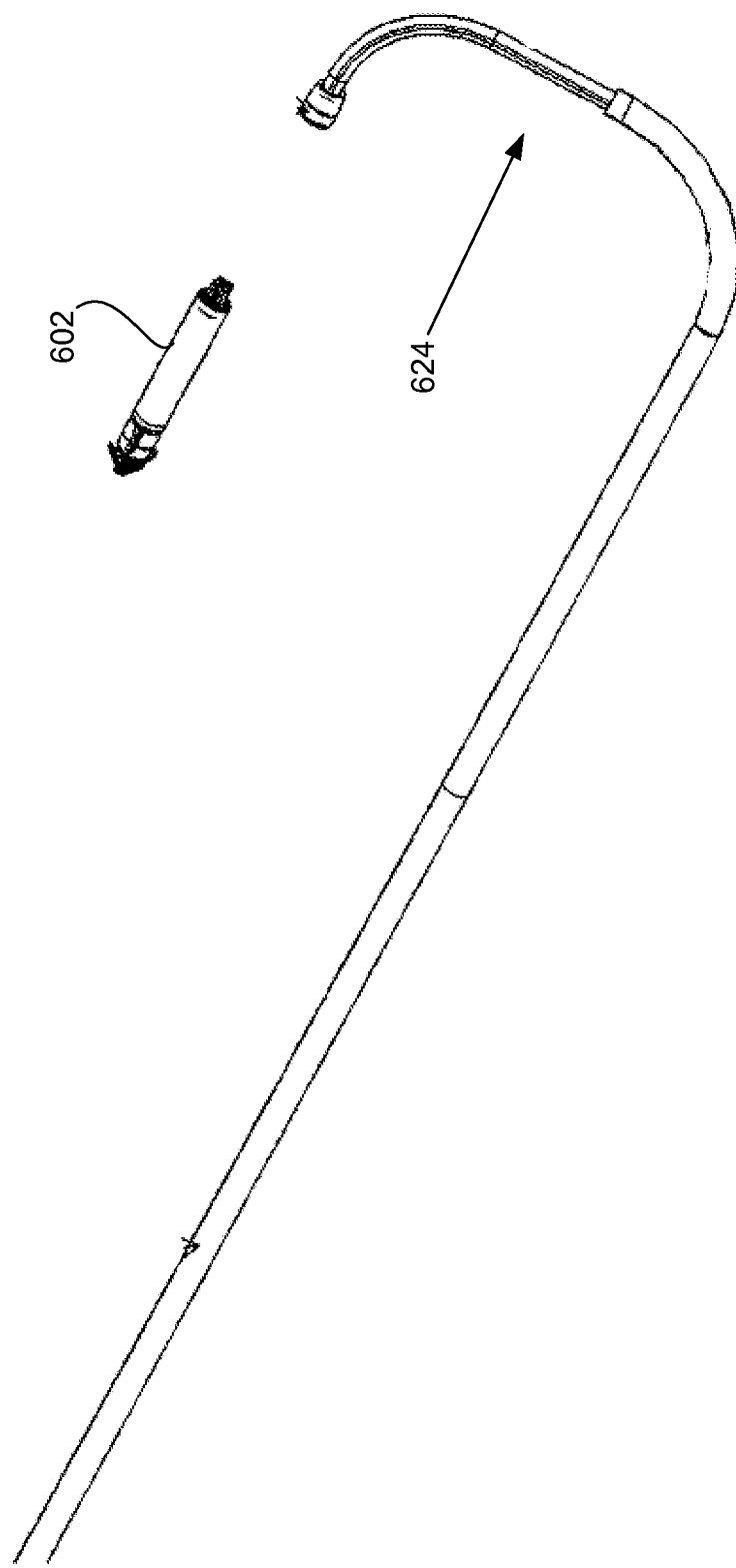

FIG. 6C is another close-up view of the distal section of a retrieval catheter with the snare retracted showing a distal curve 606 of approximately 180 degrees. In this embodiment, the 180 degree distal curve enables the retrieval catheter to be able to access pacemakers whose proximal caps are rotated 180 degrees from the point of entry of the catheter.

FIGS. 7A-7C show various views of one embodiment of a docking cap 704. The docking cap of FIGS. 7A-7C can be used in the systems described above. In FIG. 7A, a distal tip of the docking cap can include scallop features 726. As shown in FIG. 7A, the scallop features can comprise a series of curves or cutouts into the distal end of the docking cap. FIG. 7A illustrates four scallop features, however in other embodiments different numbers of scallop features can be used, such as one, two, three, or more than four scallop features. The scallop features are configured to prevent the docking cap from binding in a perpendicular configuration with a leadless pacemaker during retrieval, as will be described below. The scallop features can include not only curved cutouts, as shown, but can also be sloped or beveled inwards towards the interior of the docking cap. This feature can aid the docking cap in assuming an aligned, co-linear configuration with the medical device to be retrieved.

FIG. 7B is a cutaway view of the docking cap of FIG. 7A, and illustrates a keyed portion or interference feature 728 disposed on the inside of the docking cap 704. The keyed portion can be configured to align with or engage a matching keyed portion or feature on the medical device to be retrieved. For example, using the leadless cardiac pacemaker described above as an example, the retrieval feature of the pacemaker can include a corresponding keyed portion or feature designed to engage the keyed portion 728 of the docking cap. When the docking cap is rotated, the keyed portions can engage one another to provide additional torque to the pacemaker, such as when unscrewing the pacemaker from tissue.

FIG. 7C illustrates a perspective view of a docking cap including an interference feature 728 disposed inside the docking cap 704. FIG. 7C illustrates a retrieval feature 720 of a medical device, such as a leadless cardiac pacemaker, disposed within the docking cap and coming into contact with the interference feature 728 of the docking cap. As shown in FIG. 7C, the retrieval feature can be disposed within the docking cap at an angle, yet still engaging the interference feature of the pacemaker. As will be described in more detail below, when the retrieval feature 720 is attached to the pacemaker with a flexible stem or flexible attachment, it allows the retrieval feature to bend as it is pulled within the docking cap. This allows the docking cap to still apply rotational torque to the retrieval feature and the pacemaker via interference feature 728 even when the pacemaker is not aligned longitudinally with the retrieval catheter and docking cap.

FIG. 7D illustrates a top down view of the docking cap 704, looking into the docking portion from the distal end. As shown, the docking cap can include a recessed slot 730 sized and shaped to receive a key feature of the torque shaft (or snare locking sleeve) of the retrieval catheter. In FIG. 7C, the recessed slot 730 is illustrated as being square in shape. This recessed slot is therefore sized and configured to receive a key on the torque shaft having a square shape. It should be understood that any size or shape recessed slot can be used, and that a corresponding key feature on the torque shaft should be similarly sized and shaped to mate with the slot.

When the key feature of the torque shaft is aligned with the recessed slot 730 of the docking cap, the torque shaft is effectively coupled to the docking cap of the catheter. This coupling allows the torque shaft to apply rotational torque to the docking cap. If the torque shaft is advanced distally through the slot 730 so that the slot does not align with the key feature of the torque shaft, then the torque shaft is not coupled to the docking cap, and the two are free to rotate relative to another. Thus, when the torque shaft (also referred to herein as the snare slider) is advanced distally to close the snare, the torque shaft can become decoupled from the docking cap. When the torque shaft and snare are then pulled proximately into the docking cap, the key feature of the torque shaft can align with the slot 730 of the docking cap, allowing the torque shaft to apply torque to the docking cap to unscrew the pacemaker from tissue. The key feature of the torque shaft is also shown in FIG. 7E.

FIG. 7D also illustrates a lumen 731 disposed in the docking cap. The lumen can be, for example, a hollow portion of the torque shaft. The lumen of the torque shaft can house the snare, described above, allowing the snare to be advanced distally from the docking cap. Also as described above, when the snare is advanced distally from the docking cap, advancing the torque shaft distally over the snare can cause the loop(s) of the snare to close around a pacemaker to be retrieved.

FIG. 7E illustrates another cutaway view of the docking cap. In FIG. 7E, the torque shaft or snare locking sleeve 705 has been advanced slightly within the docking cap, illustrating key feature 733 of the torque shaft being decoupled from slot 730 of the docking cap. When the key torque shaft is decoupled from the docking cap, as described above, rotation of the torque shaft does not cause the docking cap to rotate. However, if the key feature 733 of FIG. 7E was pulled back proximally to engage slot 730 of the docking cap, then the torque shaft and docking cap would be coupled together, and rotation of the torque shaft would apply rotational torque to the docking cap.

Figure 8B:
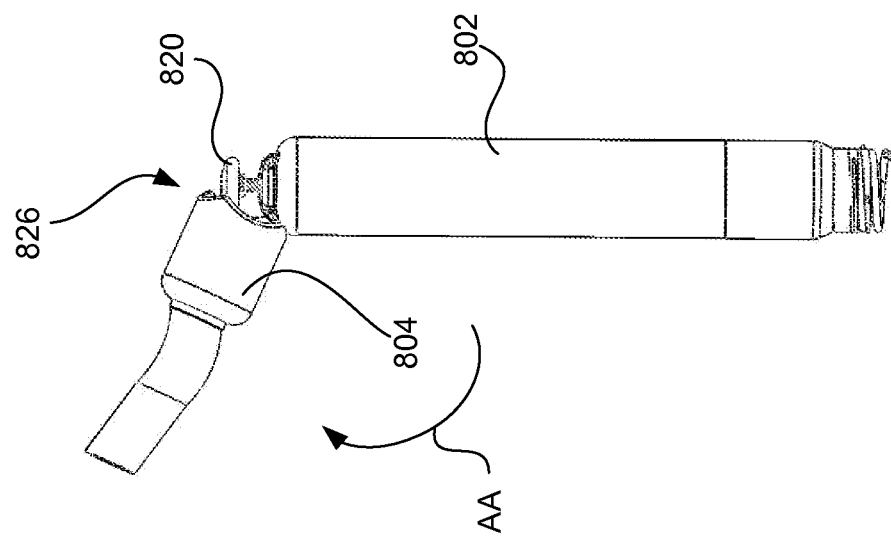
FIGS. 8A-8C show a pacemaker being retrieved by a retrieval catheter system when the catheter is not aligned with the pacemaker.
Figure 8A:
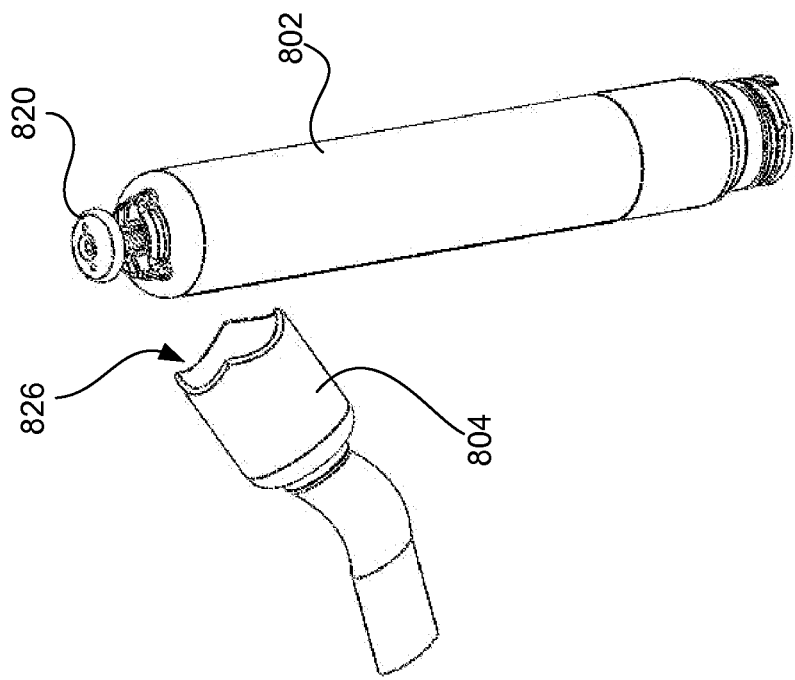
Figure 8C:
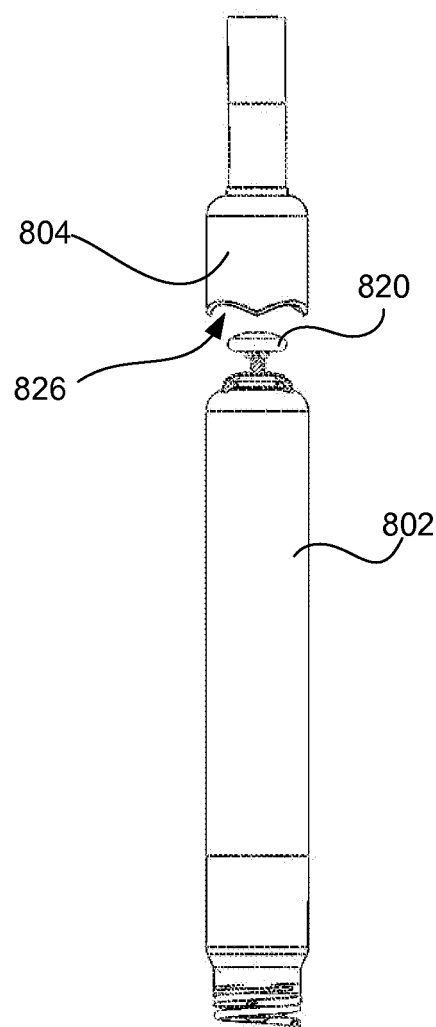

FIGS. 8A-8B illustrate various embodiments of a docking cap 804 having scallop features 826 engaging a medical device or pacemaker 802. As described above in FIG. 7A, scallop features 826 on a distal portion of the docking cap can prevent the docking cap from binding perpendicularly with a medical device during retrieval. In FIG. 8A, the retrieval catheter and docking cap 804 are shown approaching the pacemaker 802 in a substantially perpendicular configuration. The catheter is shown without the snare (as described above) for simplicity. Referring to FIG. 8B, once the snare (not shown) has grasped the retrieval feature 820 of pacemaker 802, the catheter, and docking cap 804, can swing upwards, as indicated by arrows AA, due to the scallop features 826 of the docking cap. FIG. 8C illustrates the docking cap 804 and retrieval catheter in the co-linear configuration with retrieval feature 820 of pacemaker 802, as a result of scallop features 826.

FIGS. 9A-9B and 10A-10B show multiple views of various embodiments of retrieval features on a leadless cardiac pacemaker. The retrieval features illustrated in these figures can be grasped by the snare of the retrieval catheters described herein, and can also be configured to dock within the docking cap of the retrieval catheter.

Figure 9A:
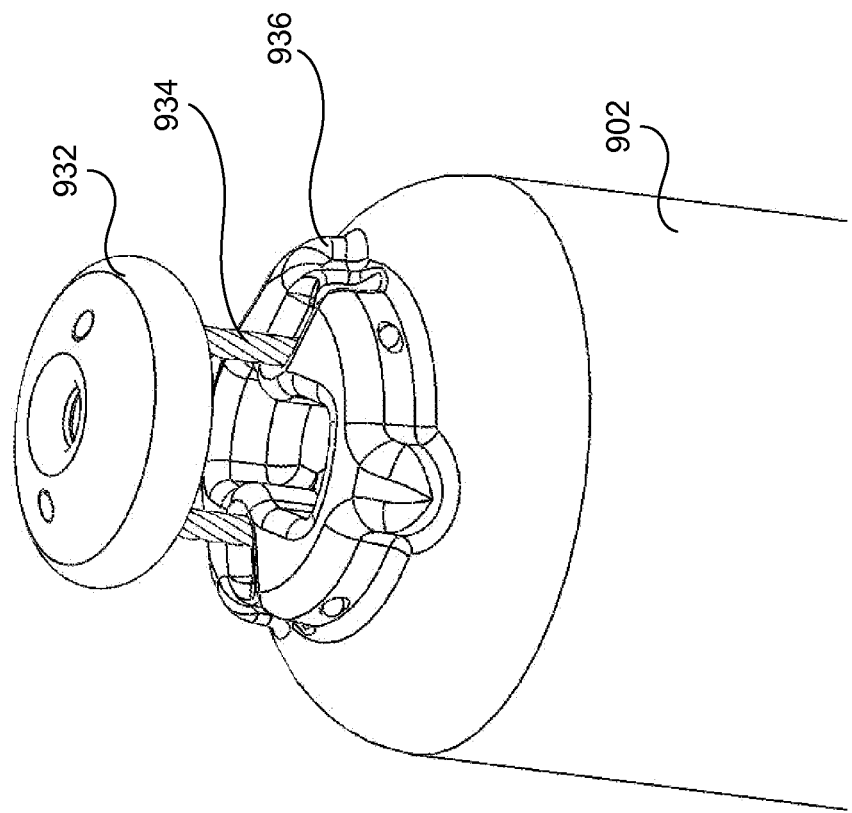
FIGS. 9A-9B are various views of one embodiment of a pacemaker having a retrieval feature.
Figure 9B:
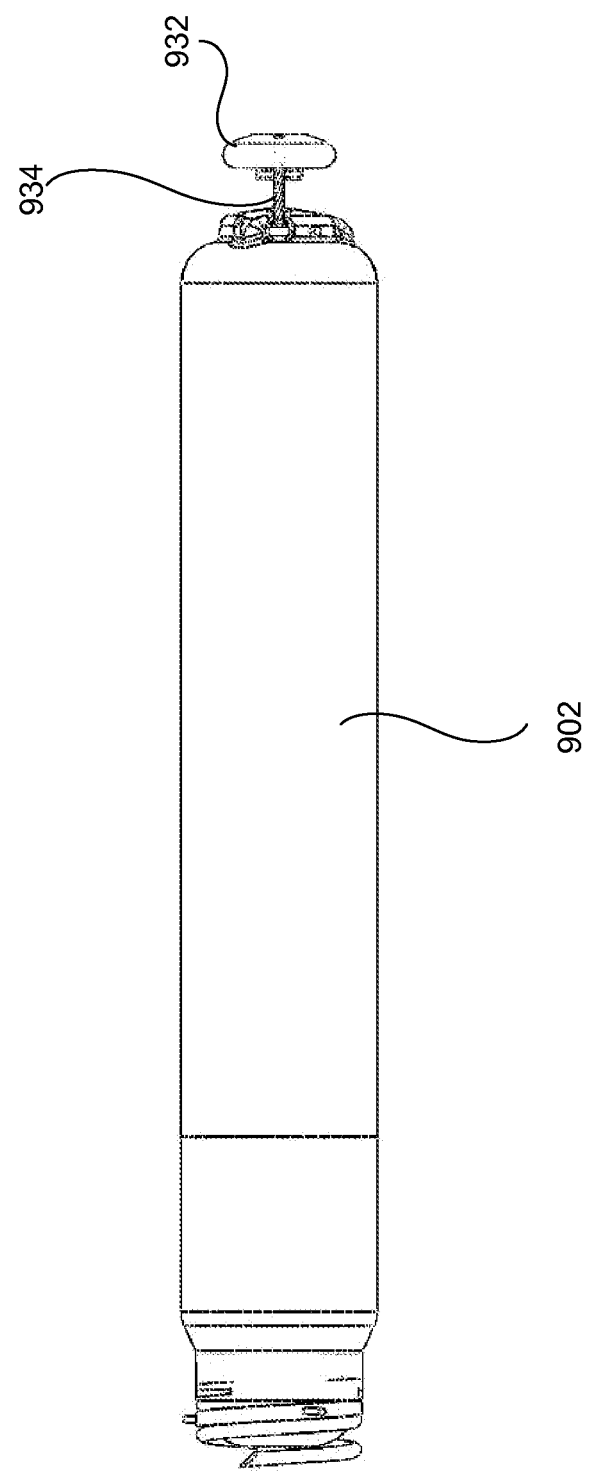

In FIGS. 9A-9B, the retrieval feature comprises a "button" or circular grasping feature 932. The grasping feature 932 can be attached to the pacemaker 902 via at least one flexible stem 934. The flexible stem allows for easier capturing of the pacemaker into the docking cap by allowing the grasping feature and stem(s) to "bend" into the docking cap when the retrieval catheter is off-axis from the pacemaker during a retrieval attempt. The flexible stem(s) also allow the grasping feature 932 to orient itself within the snare and to compensate for the asymmetry of the snare to allow it to align the docking cap with the pacemaker. Additionally, the flexible stem deflection permits torque transmission from the catheter to the leadless pacemaker. The flexible stem can be made of materials such as nitinol, stainless steel or titanium cable, MP35N, or other similar materials. The flexible stem may be connected to the grasping feature and the proximal end of the leadless pacemaker by laser welding, soldering, or other manufacturing processes know in the art.

Also shown in FIG. 9A, a proximal portion of the pacemaker 902 can include a key feature 936. The key feature 936 can be sized and configured to mate with the interference feature within the docking cap, as described above. The key feature of the pacemaker and the interference feature of the docking cap and catheter can allow the torque shaft and docking cap of the catheter to apply rotational torque to the pacemaker, such as to unscrew the pacemaker from tissue during retrieval.

Figure 10A:
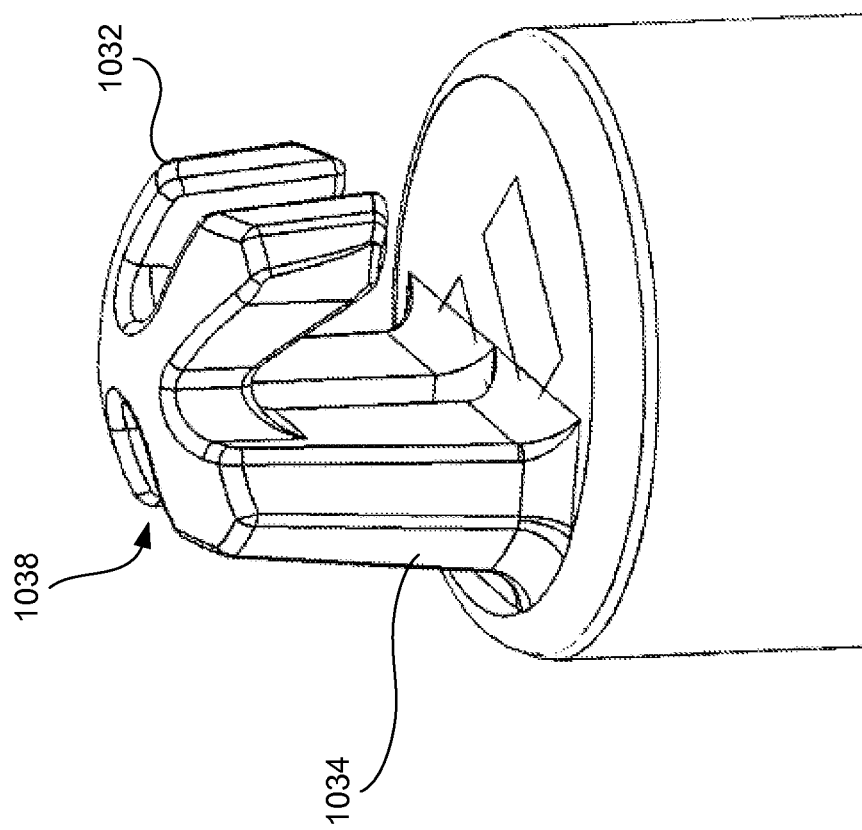
FIGS. 10A-10B are various views of another embodiment of a pacemaker having a retrieval feature.
Figure 10B:
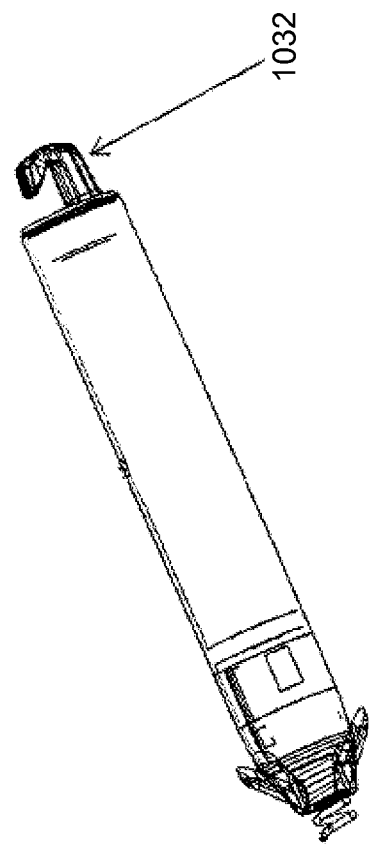

FIGS. 10A-10B illustrate another embodiment of a "hook shaped" retrieval feature 1032 on the pacemaker 1002. The hook shaped proximal cap can allow for easier grasping by the snare. The "hook shaped" retrieval feature can provide an easily accessible yet atraumatic surface for the snare to grasp. In some embodiments, a base portion 1034 of the hook shaped feature can comprise a flexible material, as described above with respect to the flexible stems of the "button" shaped retrieval feature in FIGS. 9A-9B. The hook shaped retrieval feature can also include cutouts 1038 that can serve a similar purpose to the key feature described above in FIGS. 9A-9B. The cutouts can engage, for example, similarly shaped features in the docking cap or retrieval catheter to allow the catheter to apply rotational torque to the pacemaker for unscrewing the pacemaker from tissue.

As described above, the docking cap itself can include cutouts or recessed slots configured to mate with or engage the retrieval feature of the pacemaker. For example, the circular retrieval feature of FIGS. 9A-9B can mate with a similarly shaped recessed slot within the docking cap. Similarly, the hook shaped retrieval feature of FIGS. 10A-10B can mate with a similarly shaped recessed slot within the docking cap.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A leadless pacemaker transport system, comprising:
 a catheter shaft extending along a longitudinal axis;
 a docking cap disposed on the catheter shaft and having an interior configured to receive a retrieval feature of a leadless pacemaker;
 a torque shaft disposed within the catheter shaft, wherein the torque shaft connects to the docking cap; and
 a handle having a first handle portion coupled to the catheter shaft and a second handle portion coupled to the torque shaft, wherein the first handle portion rotates relative to the second handle portion to apply rotational torque through the torque shaft to the docking cap.

2. The leadless pacemaker transport system of claim 1, wherein the docking cap is rotatable relative to the catheter shaft.

3. The leadless pacemaker transport system of claim 2 further comprising a bearing between the docking cap and the catheter shaft to allow the docking cap to rotate relative to the catheter shaft.

4. The leadless pacemaker transport system of claim 1 further comprising a snare disposed within the catheter shaft and extendable distally beyond the catheter shaft, wherein the snare includes one or more loops.

5. The leadless pacemaker transport system of claim 4, wherein the one or more loops includes a plurality of loops.

6. The leadless pacemaker transport system of claim 4, wherein the handle includes a snare slider to extend the snare beyond the catheter shaft.

7. The leadless pacemaker transport system of claim 1, wherein the handle includes a deflection knob to steer the catheter shaft.

8. A leadless pacemaker system, comprising:
   a leadless pacemaker including a retrieval feature; and
   a leadless pacemaker transport system comprising:
      a catheter shaft extending along a longitudinal axis,
      a docking cap disposed on the catheter shaft and having an interior configured to receive the retrieval feature of the leadless pacemaker,
      a torque shaft disposed within the catheter shaft, wherein the torque shaft connects to the docking cap, and
      a handle having a first handle portion coupled to the catheter shaft and a second handle portion coupled to the torque shaft, wherein the first handle portion rotates relative to the second handle portion to apply rotational torque through the torque shaft to the docking cap.

9. The leadless pacemaker system of claim 8, wherein the docking cap is rotatable relative to the catheter shaft.

10. The leadless pacemaker system of claim 9 further comprising a bearing between the docking cap and the catheter shaft to allow the docking cap to rotate relative to the catheter shaft.

11. The leadless pacemaker system of claim 8 further comprising a snare disposed within the catheter shaft and extendable distally beyond the catheter shaft, wherein the snare includes one or more loops.

12. The leadless pacemaker system of claim 11, wherein the one or more loops includes a plurality of loops.

13. The leadless pacemaker system of claim 11, wherein the handle includes a snare slider to extend the snare beyond the catheter shaft.

14. The leadless pacemaker system of claim 8, wherein the handle includes a deflection knob to steer the catheter shaft.

15. A method, comprising:
   positioning a retrieval feature of a leadless pacemaker inside an interior of a docking cap of a leadless pacemaker transport system, wherein the docking cap is disposed on a catheter shaft, and wherein a torque shaft is disposed within the catheter shaft and connects to the docking cap; and
   rotating a first handle portion of a handle relative to a second handle portion of the handle to apply rotational torque through the torque shaft to the docking cap, wherein the first handle portion is coupled to the catheter shaft and the second handle portion is coupled to the torque shaft.

16. The method of claim 15, wherein the docking cap is rotatable relative to the catheter shaft.

17. The method of claim 16 further comprising a bearing between the docking cap and the catheter shaft to allow the docking cap to rotate relative to the catheter shaft.

18. The method of claim 15 further comprising moving a snare slider of the handle to extend a snare distally beyond the catheter shaft, wherein the snare includes one or more loops.

19. The method of claim 18, wherein the one or more loops includes a plurality of loops.

20. The method of claim 15 further comprising moving a deflection knob of the handle to steer the catheter shaft.

* * * * *